US006440694B1

(12) United States Patent
Bienkowski et al.

(10) Patent No.: US 6,440,694 B1
(45) Date of Patent: Aug. 27, 2002

(54) TNF-RELATED DEATH LIGAND

(75) Inventors: Michael J. Bienkowski, Portage; Cynthia J. Mills, Kalamazoo, both of MI (US); David A. Jones, Salt Lake City, UT (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/157,864

(22) Filed: Sep. 21, 1998

Related U.S. Application Data

(60) Provisional application No. 60/060,475, filed on Sep. 30, 1997.

(51) Int. Cl.[7] .............................. C12P 21/06; C12P 1/00; A61K 38/00; C07K 2/00; C07K 4/00

(52) U.S. Cl. ........................ 435/69.1; 435/41; 435/69.5; 435/325; 530/300; 530/350; 536/1; 536/1.11; 536/18.7; 536/22.1; 536/23.1

(58) Field of Search ........................ 536/1, 1.11, 18.7, 536/22.1, 23.1; 435/41, 69.1, 69.5, 325; 530/300, 350

(56) References Cited

U.S. PATENT DOCUMENTS

| 5,344,915 A | 9/1994 | LeMaire et al. ............. 530/350 |
| 6,171,787 B1 * | 1/2001 | Wiley | |

FOREIGN PATENT DOCUMENTS

| WO | WO 95/32627 | 12/1995 | .......... A01N/37/18 |
| WO | WO 97/01633 | 1/1997 | .......... C12N/15/09 |
| WO | WO 97/12632 | 4/1997 | .......... A61K/39/00 |
| WO | WO 97/33902 | * 9/1997 | |
| WO | WO 99/00518 | 1/1999 | ............ C12Q/1/68 |

OTHER PUBLICATIONS

Sequence 1 and 2 of U.S. Patent 6,171,787. Amino acid and nucleic acid database sheets, 2001.*
Ausubel (editor) et al. Short Protocols in molecular biology, second edition. Section 1, Unit 16.1 and 16.2, 1992.*
SF Altschul, W Gish, W Miller, EW Myers, DJ Lipman, "Basic Local Alignment Search Tool," J. Mol. Biol. 215 (1990), 403–410.
VR Baichwal, PA Baeuerle, "Apoptosis: Activate NF–κB or die?" Current Biology 7 (1997), R94–R96.
AA Beg, D Baltimore, "An Essential Role for NF–κB in Preventing TNF–β–Induced Cell Death," Science, vol. 274 (1996), 782–784.
MP Boldin, TM Goncharov, YV Goltsev, D Wallach, "Involvement of MACH, a Novel MORT1/FADD–Interacting Protease, in Fas/APO–1– and TNF Receptor–Induced Cell Death," Cell, vol. 85 (1996), 803–815.

AM Chinnaiyan, K O'Rourke, G Yu, RH Lyons, M Garg, DR Duan, L Xing, R Gentz, J Ni, VM Dixit, "Signal Transduction by DR3, a Death Domain–Containing Receptor Related to TNFR–1 and CD95," Science, vol. 274 (1996), 990–992.
M Hahne, T Kataoka, M Schröter, K Hofmann, M Irmler, J Bodmer, P Schneider, T Bornand, N Holler, LE French, B Sordat, D Rimoldi, J Tschopp, "April, a New Ligand of the Tumor Necrosis Factor Family, Stimulates Tumor Cell Growth," J. Exp. Med, vol. 188, No. 6, (1998), 1185–1190.
T Idziorek, J Estaquier, F De Bels, J Ameisen, "YOPRO–1 permits cytofluorometric analysis of programmed cell death (apoptosis) without interfering with cell viability," J. Immuno. Meth. 185 (1995), 249–258.
Z Liu, H Hsu, DV Goeddel, M Karin, "Dissection of TNF Receptor 1 Effector Funtions: JNK Activation Is Not Linked to Apoptosis While NF—κB Activation Prevents Cell Death," Cell, vol. 87 (1996), 565–576.
M Muzio, et al., "FLICE, A Novel FADD–Homologous ICE/CED–3–like Protease, Is Recruited to the DC95 (Fas/APO–1) Death–Inducing Signaling Complex," Cell, vol. 85 (1996), 817–827.
G Pan, K O'Rourke, AM Chinnaiyan, R Gentz, R Ebner, J Ni, VM Dixit, "The Receptor for the Cytotoxic Ligand TRAIL," Science, vol. 276 (1997), 111–113.
DJ Van Antwerp, SJ Martin, T Kafri, DR Green, IM Verma, "Suppression of TNF–β–Induced Apoptosis by NF–κB," Science, vol. 274 (1996), 787–789.
C Wang, NW Mayo, AS Baldwin, "TNF– and Cancer Therapy–Induced Apoptosis: Potentiation by Inhibition of NF–κB," Science, vol. 274 (1996), 784–789.
XM Wang, PI Terasaki, GW Rankin, D Chia, HP Zhong, S Hardy, "A New Microcellular Cytotoxicity Test Based on Calcein AM Release," Human Immunology 37 (1993), 264–270.
SR Wiley, et al., "Identification and Characterization of a New Member of the TNF Family that Induces Apoptosis," Immunity, vol. 3 (1995), 673–682.
M Wu, et al., "Inhibition of NF–κB/Rel induces apoptosis of murines B cells," EMBO J 15, (1996), 4682–4690.

* cited by examiner

*Primary Examiner*—Anthony G. Caputa
*Assistant Examiner*—Alana M. Harris
(74) *Attorney, Agent, or Firm*—Edward F. Rehberg; Thomas A. Wootton; Lori L. Kerber

(57) ABSTRACT

The invention relates to a novel tumor necrosis factor (TNF) homolog designated herein as TNF-related death ligand (TRDL). Isolated nucleic acid molecules are provided which encode TRDL. TRDL polypeptides are also provided, as are methods for identifying agonists and antagonists of TRDL activity.

19 Claims, 12 Drawing Sheets

TNfα: 191 YEPIYLGGVFQLEKGDRLSAEINR 214
       |   |  ||| | +|| ||  | |
78258: 158 YNXCYXAGVFHLHQGDILSVIIPR 229

FIG. 1A

TNfα: 126 VPSEGLYLIYSQVLFK 141
       +    |+||+| ||||+
78258:   5 IQDAGVYLLYRQVLFQ 52

FIG. 1B

```
           TTTCAGGTCCCGGATCCGCGCTTGCTACCCCACTCTTGAAACCACAGCTGTTGGCAGGGT
     CCCCAGCTCATGCCAGCCTCATCTCCTTTCTTGCTAGCCCCCAAAGGGCCTCCAGGCAAC
 1             M  P  A  S  S  P  F  L  L  A  P  K  G  P  P  G  N      17
     ATGGGGGGCCCAGTCAGAGAGCCGGCACTCTCAGTTGCCCTCTGGTTGAGTTGGGGGGCA
 18  M  G  G  P  V  R  E  P  A  L  S  V  A  L  W  L  S  W  G  A       37
     GCTCTGGGGGCCGTGGCTTGTGCCATGGCTCTGCTGACCCAACAAACAGAGCTGCAGAGC
 38  A  L  G  A  V  A  C  A  M  A  L  L  T  Q  Q  T  E  L  Q  S       57
     CTCAGGAGAGAGGTGAGCCGGCTGCAGGGGACAGGAGGCCCCTCCCAGAATGGGGAAGGG
 58  L  R  R  E  V  S  R  L  Q  G  T  G  G  P  S  Q  N  G  E  G       77
     TATCCCTGGCAGAGTCTCCCGGAGCAGAGTTCCGATGCCCTGGAAGCCTGGGAGAGTGGG
 78  Y  P  W  Q  S  L  P  E  Q  S  S  D  A  L  E  A  W  E  S  G       97
     GAGAGATCCCGGAAAAGGAGAGCAGTGCTCACCCAAAAACAGAAGAATGACTCCGATGTG
 98  E  R  S  R  K  R  R  A  V  L  T  Q  K  Q  K  N  D  S  D  V      117
     ACAGAGGTGATGTGGCAACCAGCTCTTAGGCGTGGGAGAGGCCTACAGGCCCAAGGATAT
118  T  E  V  M  W  Q  P  A  L  R  R  G  R  G  L  Q  A  Q  G  Y      137
     GGTGTCCGAATCCAGGATGCTGGAGTTTATCTGCTGTATAGCCAGGTCCTGTTTCAAGAC
138  G  V  R  I  Q  D  A  G  V  Y  L  L  Y  S  Q  V  L  F  Q  D      157
     GTGACTTTCACCATGGGTCAGGTGGTGTCTCGAGAAGGCCAAGGAAGGCAGGAGACTCTA
158  V  T  F  T  M  G  Q  V  V  S  R  E  G  Q  G  R  Q  E  T  L      177
     TTCCGATGTATAAGAAGTATGCCCTCCCACCCGGACCGGGCCTACAACAGCTGCTATAGC
178  F  R  C  I  R  S  M  P  S  H  P  D  R  A  Y  N  S  C  Y  S      197
     GCAGGTGTCTTCCATTTACACCAAGGGGATATTCTGAGTGTCATAATTCCCCGGGCAAGG
198  A  G  V  F  H  L  H  Q  G  D  I  L  S  V  I  I  P  R  A  R      217
     GCGAAACTTAACCTCTCTCCACATGGAACCTTCCTGGGGTTTGTGAAACTGTGATTGTGT
218  A  K  L  N  L  S  P  H  G  T  F  L  G  F  V  K  L              234
     TATAAAAAGTGGCTCCCAGCTTGGAAGACCAGGGTGGGTACATACTGGAGACAGCCAAGA
     GCTGAGTATATAAAGGAGAGGGAATGTGCAGGAACAGAGGCGTCTTCCTGGGTTTGGCTC
     CCCGTTCCTCACTTTTCCCTTTTCATTCCCACCCCCTAGACTTTGATTTTACGGATATCT
     TGCTTCTGTTCCCCATGGAGCTCCGAATTCTTGCGTGTGTGTAGATGAGGGGCGGGGACG
     GGCGCCAGGCATTGTCCAGACCTGGTCGGGCCCACTGGAAGCATCCAGAACAGCACCACC
     ATCTAGCGGCCGCTCGAGGGAAGCACCCGCCGGTTGGCCGAAGTCCACGAAGCCGCCCTC
     TGCTAGGGAAAACCCCTGGTTCTCCATGCCACACCTCTCTCCAGGTGCCCTCTGCCTCTT
     CACCCCACAAGAAGCCTTATCCTACGTCCTTCTCTCCATCTATCGGACCCCAGTTTCCAT
     CACTATCTCCAGAGATGTAGCTATTATGCGCCCGTCTACAGGGGGTGCCCGACGATGACG
     GTGCCTTCGCAGTCAAATTACTCTTCGGGTCCCAAGGTTTGGCTTTCACGCGCTCCATTG
     CCCCGGCGTGGCAGGCCATTCCAAGCCCTTCCGGGCTGGAACTGGTGTCGGAGGAGCCTC
     GGGTGTATCGTACGCCCTGGTGTTGGTGTTGCCTCACTCCTCTGAGCTCTTCTTTCTGAT
     CAAGCCCTGCTTAAAGTTAAATAAAATAGAATGAATGATAAAAAAAAAAAAAAA
```

FIG. 3

```
                TTTTATTTCAGGTCCCGGATCCGCGCTTGAAACCACAGCTGTTGGCAGGGTCCCCAGCTC
                ATGCCAGCCTCATCTCCTTTCTTGCTAGCCCCCAAAGGGCCTCCAGGCAACATGGGGGGC
  1             M  P  A  S  S  P  F  L  L  A  P  K  G  P  P  G  N  M  G  G       20
                CCAGTCAGAGAGCCGGCACTCTCAGTTGCCCTCTGGTTGAGTTGGGGGGCAGCTCTGGGG
 21             P  V  R  E  P  A  L  S  V  A  L  W  L  S  W  G  A  A  L  G       40
                GCCGTGGCTTGTGCCATGGCTCTGCTGACCCAACAAACAGAGCTGCAGAGCCTCAGGAGA
 41             A  V  A  C  A  M  A  L  L  T  Q  Q  T  E  L  Q  S  L  R  R       60
                GAGGTGAGCCGGCTGCAGGGGACAGGAGGCCCCTCCCAGAATGGGGAAGGGTATCCCTGG
 61             E  V  S  R  L  Q  G  T  G  G  P  S  Q  N  G  E  G  Y  P  W       80
                CAGAGTCTCCCGGAGCAGAGTTCCGATGCCCTGGAAGCCTGGGAGAATGGGGAGAGATCC
 81             Q  S  L  P  E  Q  S  S  D  A  L  E  A  W  E  N  G  E  R  S      100
                CGGAAAAGGAGAGCAGTGCTCACCCAAAAACAGAAGAAGCAGCACTCTGTCCTGCACCTG
101             R  K  R  R  A  V  L  T  Q  K  Q  K  K  Q  H  S  V  L  H  L      120
                GTTCCCATTAACGCCACCTCCAAGGATGACTCCGATGTGACAGAGGTGATGTGGCAACCA
121             V  P  I  N  A  T  S  K  D  D  S  D  V  T  E  V  M  W  Q  P      140
                GCTCTTAGGCGTGGGAGAGGCCTACAGGCCCAAGGATATGGTGTCCGAATCCAGGATGCT
141             A  L  R  R  G  R  G  L  Q  A  Q  G  Y  G  V  R  I  Q  D  A      160
                GGAGTTTATCTGCTGTATAGCCAGGTCCTGTTTCAAGACGTGACTTTCACCATGGGTCAG
161             G  V  Y  L  L  Y  S  Q  V  L  F  Q  D  V  T  F  T  M  G  Q      180
                GTGGTGTCTCGAGAAGGCCAAGGAAGGCAGGAGACTCTATTCCGATGTATAAGAAGTATG
181             V  V  S  R  E  G  Q  G  R  Q  E  T  L  F  R  C  I  R  S  M      200
                CCCTCCCACCCGGACCGGGCCTACAACAGCTGCTATAGCGCAGGTGTCTTCCATTTACAC
201             P  S  H  P  D  R  A  Y  N  S  C  Y  S  A  G  V  F  H  L  H      220
                CAAGGGGATATTCTGAGTGTCATAATTCCCCGGGCAAGGGCGAAACTTAACCTCTCTCCA
221             Q  G  D  I  L  S  V  I  I  P  R  A  R  A  K  L  N  L  S  P      240
                CATGGAACCTTCCTGGGACTTTGATTTTACGGATATCTTGCTTCTGTTCCCCATGGAGCT
241             H  G  T  F  L  G  L                                             247
                CCGAATTCTTGCGTGTGTGTAGATGAGGGGCGGGGGACGGGCGCCAGGCATTGTTCAGAC
                CTGGTCGGGGCCCACTGGAAGCATCCAGAACAGCACCACCATCTAGCGGCCGCTCGAGGG
                AAGCACCCGCCGGTTGGCCGAAGTCCACGAAGCCGCCCTCTGCTAGGGAAAACCCCTGGT
                TCTCCATGCCACACCTCTCTCCAGGTGCCCTCTGCCTCTTCACCCCACAAGAAGCCTTAT
                CCTACGTCCTTCTCTCCATCTATCGGACCCAGTTTCCATCACTATCTCCAGAGATGTAG
                CTATTATGCGCCCGTCTACAGGGGGTGCCCGACGATGACGGTGCCTTCGCAGTCAAATTA
                CTCTTCGGGTCCCAAGGTTTGGCTTTCACGCGCTCCATTGCCCCGGCGTGGCAGGCCATT
                CCAAGCCCTTCCGGGCTGGAACTGGTGTCGGAGGAGCCTCGGGTGTATCGTACGCCCTGG
                TGTTGGTGTTGCCTCACTCCTCTGAGCTCTTCTTTCTGATCAAGCCCTGCTTAAAGTTAA
                ATAAAATAGAATGAATGATAAAAAAAAAAAAAAAAAAAAAAAAAAAAAA
```

FIG. 4

```
  1 .....TTTCAGGTCCCGGATCCGCGCTTGCTACCCCACTCTTGAAACCAC  45
       |||||||||||||||||||||||                |||||||||||
  1 TTTTATTTCAGGTCCCGGATCCGCG.............CTTGAAACCAC  36

46 AGCTGTTGGCAGGGTCCCCAGCTCATGCCAGCCTCATCTCCTTTCTTGCT  95
    |||||||||||||||||||||||||||||||||||||||||||||||||||
 37 AGCTGTTGGCAGGGTCCCCAGCTCATGCCAGCCTCATCTCCTTTCTTGCT  86

96 AGCCCCCAAAGGGCCTCCAGGCAACATGGGGGGCCCAGTCAGAGAGCCGG 145
    |||||||||||||||||||||||||||||||||||||||||||||||||||
 87 AGCCCCCAAAGGGCCTCCAGGCAACATGGGGGGCCCAGTCAGAGAGCCGG 136

146 CACTCTCAGTTGCCCTCTGGTTGAGTTGGGGGGCAGCTCTGGGGGCCGTG 195
    |||||||||||||||||||||||||||||||||||||||||||||||||||
137 CACTCTCAGTTGCCCTCTGGTTGAGTTGGGGGGCAGCTCTGGGGGCCGTG 186

196 GCTTGTGCCATGGCTCTGCTGACCCAACAAACAGAGCTGCAGAGCCTCAG 245
    |||||||||||||||||||||||||||||||||||||||||||||||||||
187 GCTTGTGCCATGGCTCTGCTGACCCAACAAACAGAGCTGCAGAGCCTCAG 236

246 GAGAGAGGTGAGCCGGCTGCAGGGGACAGGAGGCCCCTCCCAGAATGGGG 295
    |||||||||||||||||||||||||||||||||||||||||||||||||||
237 GAGAGAGGTGAGCCGGCTGCAGGGGACAGGAGGCCCCTCCCAGAATGGGG 286

296 AAGGGTATCCCTGGCAGAGTCTCCCGGAGCAGAGTTCCGATGCCCTGGAA 345
    |||||||||||||||||||||||||||||||||||||||||||||||||||
287 AAGGGTATCCCTGGCAGAGTCTCCCGGAGCAGAGTTCCGATGCCCTGGAA 336

346 GCCTGGGAGAGTGGGGAGAGATCCCGGAAAAGGAGAGCAGTGCTCACCCA 395
    ||||||||||||| |||||||||||||||||||||||||||||||||||||
337 GCCTGGGAGAATGGGGAGAGATCCCGGAAAAGGAGAGCAGTGCTCACCCA 386

396 AAAACAGAAGA................................. 406
    |||||||||||
387 AAAACAGAAGAAGCAGCACTCTGTCCTGCACCTGGTTCCCATTAACGCCA 436

407 .........ATGACTCCGATGTGACAGAGGTGATGTGGCAACCAGCTCTT 447
             ||||||||||||||||||||||||||||||||||||||||
437 CCTCCAAGGATGACTCCGATGTGACAGAGGTGATGTGGCAACCAGCTCTT 486

448 AGGCGTGGGAGAGGCCTACAGGCCCAAGGATATGGTGTCCGAATCCAGGA 497
    |||||||||||||||||||||||||||||||||||||||||||||||||||
487 AGGCGTGGGAGAGGCCTACAGGCCCAAGGATATGGTGTCCGAATCCAGGA 536

498 TGCTGGAGTTTATCTGCTGTATAGCCAGGTCCTGTTTCAAGACGTGACTT 547
    |||||||||||||||||||||||||||||||||||||||||||||||||||
537 TGCTGGAGTTTATCTGCTGTATAGCCAGGTCCTGTTTCAAGACGTGACTT 586

548 TCACCATGGGTCAGGTGGTGTCTCGAGAAGGCCAAGGAAGGCAGGAGACT 597
    |||||||||||||||||||||||||||||||||||||||||||||||||||
587 TCACCATGGGTCAGGTGGTGTCTCGAGAAGGCCAAGGAAGGCAGGAGACT 636

598 CTATTCCGATGTATAAGAAGTATGCCCTCCCACCCGGACCGGGCCTACAA 647
    |||||||||||||||||||||||||||||||||||||||||||||||||||
637 CTATTCCGATGTATAAGAAGTATGCCCTCCCACCCGGACCGGGCCTACAA 686

648 CAGCTGCTATAGCGCAGGTGTCTTCCATTTACACCAAGGGGATATTCTGA 697
    |||||||||||||||||||||||||||||||||||||||||||||||||||
687 CAGCTGCTATAGCGCAGGTGTCTTCCATTTACACCAAGGGGATATTCTGA 736
```

FIG. 5A

```
 698 GTGTCATAATTCCCCGGGCAAGGGCGAAACTTAACCTCTCTCCACATGGA  747
     ||||||||||||||||||||||||||||||       ||||||||||||
 737 GTGTCATAATTCCCCGGGCAAGGGCGAAACTTAACCTCTCTCCACATGGA  786

748 ACCTTCCTGGGGTTTGTGAAACTGTGATTGTGTTATAAAAAGTGGCTCCC  797
     ||||||||||
 787 ACCTTCCTGG......................................  796

898 CTCCCCGTTCCTCACTTTTCCCTTTTCATTCCCACCCCCTAGACTTTGAT  947
                                               |||||||||
 797 ........................................GACTTTGAT  805

948 TTTACGGATATCTTGCTTCTGTTCCCCATGGAGCTCCGAATTCTTGCGTG  997
     ||||||||||||||||||||||||||||||||||||||||||||||||||
 806 TTTACGGATATCTTGCTTCTGTTCCCCATGGAGCTCCGAATTCTTGCGTG  855

998 TGTGTAGATGAGGGGC.GGGGACGGGCGCCAGGCATTGTCCAGACCTGGT 1046
     ||||||||||||||||  ||||||||||||||||||| ||||||||||
 856 TGTGTAGATGAGGGGCGGGGGACGGGCGCCAGGCATTGTTCAGACCTGGT  905

1047 C.GGGCCCACTGGAAGCATCCAGAACAGCACCACCATCTAGCGGCCGCTC 1095
      |||||||||||||||||||||||||||||||||||||||||||||||
 906 CGGGGCCCACTGGAAGCATCCAGAACAGCACCACCATCTAGCGGCCGCTC  955

1096 GAGGGAAGCACCCGCCGGTTGGCCGAAGTCCACGAAGCCGCCCTCTGCTA 1145
     ||||||||||||||||||||||||||||||||||||||||||||||||||
 956 GAGGGAAGCACCCGCCGGTTGGCCGAAGTCCACGAAGCCGCCCTCTGCTA 1005

1146 GGGAAAACCCCTGGTTCTCCATGCCACACCTCTCTCCAGGTGCCCTCTGC 1195
     ||||||||||||||||||||||||||||||||||||||||||||||||||
1006 GGGAAAACCCCTGGTTCTCCATGCCACACCTCTCTCCAGGTGCCCTCTGC 1055

1196 CTCTTCACCCCACAAGAAGCCTTATCCTACGTCCTTCTCTCCATCTATCG 1245
     ||||||||||||||||||||||||||||||||||||||||||||||||||
1056 CTCTTCACCCCACAAGAAGCCTTATCCTACGTCCTTCTCTCCATCTATCG 1105

1246 GACCCCAGTTTTCCATCACTATCTCCAGAGATGTAGCTATTATGCGCCCGT 1295
     ||||||||||||||||||||||||||||||||||||||||||||||||||
1106 GACCCCAGTTTTCCATCACTATCTCCAGAGATGTAGCTATTATGCGCCCGT 1155

1296 CTACAGGGGGTGCCCGACGATGACGGTGCCTTCGCAGTCAAATTACTCTT 1345
     ||||||||||||||||||||||||||||||||||||||||||||||||||
1156 CTACAGGGGGTGCCCGACGATGACGGTGCCTTCGCAGTCAAATTACTCTT 1205

1346 CGGGTCCCAAGGTTTGGCTTTCACGCGCTCCATTGCCCCGGCGTGGCAGG 1395
     ||||||||||||||||||||||||||||||||||||||||||||||||||
1206 CGGGTCCCAAGGTTTGGCTTTCACGCGCTCCATTGCCCCGGCGTGGCAGG 1255

1396 CCATTCCAAGCCCTTCCGGGCTGGAACTGGTGTCGGAGGAGCCTCGGGTG 1445
     ||||||||||||||||||||||||||||||||||||||||||||||||||
1256 CCATTCCAAGCCCTTCCGGGCTGGAACTGGTGTCGGAGGAGCCTCGGGTG 1305

1446 TATCGTACGCCCTGGTGTTGGTGTTGCCTCACTCCTCTGAGCTCTTCTTT 1495
     ||||||||||||||||||||||||||||||||||||||||||||||||||
1306 TATCGTACGCCCTGGTGTTGGTGTTGCCTCACTCCTCTGAGCTCTTCTTT 1355

1496 CTGATCAAGCCCTGCTTAAAGTTAAATAAAATAGAATGAATGATAAAAAA 1545
     ||||||||||||||||||||||||||||||||||||||||||||||||||
1356 CTGATCAAGCCCTGCTTAAAGTTAAATAAAATAGAATGAATGATAAAAAA 1405

1546 AAAAAAAA................ 1554
```

FIG. 5B

```
         1                                                         50
TRDL-11  ..........  ..........  ..........  ..........  ..........
TRDL-14  ..........  ..........  ..........  ..........  ..........
   TNFa  ..........  ..........  ..........  ..........  ..........
   FasL  MQQPFNYPYP  QIYWVDSSAS  SPWAPPGTVL  PCPTSVPRRP  GQRPPPPPPP
  TRAIL  ..........  ..........  ..........  ..........  ..........

51                                                       100
TRDL-11  ......MPAS  SPFLLAPKGP  PGNMGGPV.R  EPALSVALWL  SWGAALGAVA
TRDL-14  ......MPAS  SPFLLAPKGP  PGNMGGPV.R  EPALSVALWL  SWGAALGAVA
   TNFa  .MSTESMIRD  VELAEEALPK  .KTGGPQG.S  RRCLFLSLFS  FLI..VAGAT
   FasL  PPPLPPPPPP  PPLPPLPLPP  LKKRGNHS.T  GLCLLVMFFM  VLVALVGLGL
  TRAIL  ..........  .......MAM  MEVQGGPSLG  QTCVLIVIFT  VLLQSLCVAV 101                                                      150
TRDL-11  CAMALLTQQT  ELQS......  ....LRREVS  RLQGTGGPSQ  NGEGYPWQSL
TRDL-14  CAMALLTQQT  ELQS......  ....LRREVS  RLQGTGGPSQ  NGEGYPWQSL
   TNFa  TLFCLLHFGV  IGPQ......  ....REESPR  DLSLISPLAQ  AVRS......
   FasL  GMFQLFHLQK  ELAE......  ....LRESTS  QMHTASSLEK  QIGH......
  TRAIL  TYVYFTNELK  QMQDKYSKSG  IACFLKEDDS  YWDPNDEESM  NSPCWQVKWQ 151                                                      200
TRDL-11  PEQSSDALEA  WESGER....  ..........  .....SRKRR  AVLTQKQ...
TRDL-14  PEQSSDALEA  WENGER....  ..........  .....SRKRR  AVLTQKQKKQ
   TNFa  ........SS  RTPSDK....  ..........  ......PV..  AHVVAN....
   FasL  ........PS  PPPEKK....  ..........  .....ELRKV  AHLTGK....
  TRAIL  LRQLVRKMIL  RTSEETISTV  QEKQQNISPL  VRERGPQRVA  AHITGTRGRS 201                                                      250
TRDL-11  ..........  ...KNDSDVT  EVMWQPALRR  GRGLQAQGYG  VRIQDAGVYL
TRDL-14  HSVLHLVPIN  ATSKDDSDVT  EVMWQPALRR  GRGLQAQGYG  VRIQDAGVYL
   TNFa  ..........  ..PQAEGQLQ  WLNRRANALL  ANGVELRDNQ  LVVPSEGLYL
   FasL  ..........  ..SNSRSMPL  EWEDTYGIVL  LSGVKYKKGG  LVINETGLYF
  TRAIL  NTLSSPNSKN  EKALGRKINS  WESSRSGHSF  LSNLHLRNGE  LVIHEKGFYY 251                                                      300
TRDL-11  LYSQVLFQDV  TFTMGQVVSR  EGQGR...QE  TLFRCIRSMP  SHPDRAY...
TRDL-14  LYSQVLFQDV  TFTMGQVVSR  EGQGR...QE  TLFRCIRSMP  SHPDRAY...
   TNFa  IYSQVLFKGQ  GCPSTHVLLT  HTISR...IA  VSYQTKVNLL  SAIKSPCQRE
   FasL  VYSKVYFRGQ  SC..NNLPLS  HKVYM...RN  SKYPQDLVMM  EGKMMSY...
  TRAIL  IYSQTYFRFQ  EEIKENTKND  KQMVQYIYKY  TSYPDPILLM  KSARNSCWSK 301                                                      350
TRDL-11  ..........  .NSCYSAGVF  HLHQGDILSV  IIPRARAKLN  LSPHGTFLGF
TRDL-14  ..........  .NSCYSAGVF  HLHQGDILSV  IIPRARAKLN  LSPHGTFLGL
   TNFa  TPEGAEAKPW  YEPIYLGGVF  QLEKGDRLSA  EINRPDYLDF  AESGQVYFGI
   FasL  ...CTTGQMW  ARSSYLGAVF  NLTSADHLYV  NVSELSLVNF  EES.QTFFGL
  TRAIL  DAEYG.....  LYSIYQGGIF  ELKENDRIFV  SVTNEHLID.  MDHEASFFGA

351
TRDL-11  VKL*
TRDL-14  *...
   TNFa  IAL.
   FasL  YKL.
  TRAIL  FLVG
```

FIG. 6

Electronic Northern for Clone: 177393

| Library | Lib Description | Abun | Pct Abun |
|---|---|---|---|
| TLYMNOT01 | lymphocytes (non-adher PBMNC), 24 M | 1 | 0.1070 |
| BLADNOT01 | bladder, 78 F | 3 | 0.1051 |
| LUNGNOT14 | lung, 47 M | 4 | 0.1037 |
| THYRNOT02 | thyroid, hyperthyroidism, 16 F | 2 | 0.0607 |
| KIDNTUT13 | kidney tumor, carcinoma, 51 F | 2 | 0.0529 |
| BLADNOT05 | bladder, 60 M, match to BLADTUT04 | 2 | 0.0528 |
| COLNNOT23 | colon, ulcerative colitis, 16 M | 2 | 0.0528 |
| LUNGTUT11 | lung tumor, carcinoma, 57 M | 2 | 0.0475 |
| SINIUCT01 | small intestine, ileum, 42 M | 1 | 0.0299 |
| NPOLNOT01 | nasal polyp, 78 M | 1 | 0.0286 |
| UTRSNOT05 | uterus, 45 F | 1 | 0.0278 |
| UTRSNOT11 | uterus, myometrium, 43 F | 1 | 0.0277 |
| SINTNOT13 | sm intest, ileum, ulcerative colitis, 25F | 1 | 0.0275 |
| PROSTUT10 | prostate tumor, 66 M, match to PROSNOT15 | 1 | 0.0268 |
| LEUKNOT03 | white blood cells, 27 F | 1 | 0.0262 |
| SINTFET03 | small intestine, fetal F | 2 | 0.0259 |
| PANCTUT01 | pancreatic tumor, 65 F, match to PANCNOT08 | 1 | 0.0258 |
| SKINBIT01 | skin, leg, erythema nodosum | 1 | 0.0256 |
| SCORNOT01 | spinal cord, 71 M | 1 | 0.0201 |
| LUNGNOT03 | lung, 79 M, match to LUNGTUT02 | 1 | 0.0200 |
| LUNGTUT02 | lung tumor, metas, 79 M, match to LUNGNOT03 | 1 | 0.0189 |
| BRSTTUT02 | breast tumor, 54 F, match to BRSTNOT03 | 1 | 0.0140 |
| OVARTUT01 | ovarian tumor, 43 F, match to OVARNOT03 | 1 | 0.0103 |
| BRSTNOT04 | breast, 62 F | 1 | 0.0096 |
| LUNGAST01 | lung, asthma, 17 M | 1 | 0.0094 |
| PROSNON01 | prostate, 28 M, NORM | 1 | 0.0094 |
| BRAITUT02 | brain tumor, metastasis, 58 M | 1 | 0.0075 |
| NGANNOT01 | ganglioneuroma, 9 M | 1 | 0.0073 |

Electronic Northern for Clone: 798247

| Library | Lib Description | Abun | Pct Abun |
|---|---|---|---|
| COLNNOT19 | large intestine, cecum, 18 F | 3 | 0.0878 |
| THPINOB01 | THP-1 promonocyte cell line, control | 2 | 0.0657 |
| BRAITUT07 | brain tumor, left frontal, 32 M | 2 | 0.0517 |
| PROSNOT02 | prostate, 50 M, match to PROSTUT01 | 1 | 0.0435 |
| TONSNOT01 | tonsil, hyperplasia, 6 M | 1 | 0.0339 |
| UCMCNOT02 | mononuclear cells | 1 | 0.0236 |
| SYNORAB01 | synovium, hip, rheumatoid, 68 F | 1 | 0.0195 |
| SYNOOAT01 | synovium, knee, osteoarthritis, 82 F | 1 | 0.0180 |
| OVARNOT03 | ovary, 43 F, match to OVARTUT01 | 1 | 0.0167 |
| BRAITUT02 | brain tumor, metastasis, 58 M | 2 | 0.0149 |
| EOSIHET02 | eosinophils, hypereosinophilia, 48 M | 1 | 0.0105 |
| UTRPNOM01 | uterus, F, NORM, WM | 1 | 0.0101 |
| PANCTUT02 | pancreatic tumor, carcinoma, 45 F | 1 | 0.0086 |
| UCMCL5T01 | mononuclear cells, treated IL-5 | 1 | 0.0084 |

FIG. 7

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 1550 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:1:

| | | | | | |
|---|---|---|---|---|---|
| TTTCAGGTCC | CGGATCCGCG | CTTGCTACCC | CACTCTTGAA | ACCACAGCTG | TTGGCAGGGT | 60 |
| CCCCAGCTCA | TGCCAGCCTC | ATCTCCTTTC | TTGCTAGCCC | CCAAAGGGCC | TCCAGGCAAC | 120 |
| ATGGGGGGCC | CAGTCAGAGA | GCCGGCACTC | TCAGTTGCCC | TCTGGTTGAG | TTGGGGGGCA | 180 |
| GCTCTGGGGG | CCGTGGCTTG | TGCCATGGCT | CTGCTGACCC | AACAAACAGA | GCTGCAGAGC | 240 |
| CTCAGGAGAG | AGGTGAGCCG | GCTGCAGGGG | ACAGGAGGCC | CCTCCCAGAA | TGGGGAAGGG | 300 |
| TATCCCTGGC | AGAGTCTCCC | GGAGCAGAGT | TCCGATGCCC | TGGAAGCCTG | GGAGAGTGGG | 360 |
| GAGAGATCCC | GGAAAAGGAG | AGCAGTGCTC | ACCCAAAAAC | AGAAGAATGA | CTCCGATGTG | 420 |
| ACAGAGGTGA | TGTGGCAACC | AGCTCTTAGG | CGTGGGAGAG | GCCTACAGGC | CCAAGGATAT | 480 |
| GGTGTCCGAA | TCCAGGATGC | TGGAGTTTAT | CTGCTGTATA | GCCAGGTCCT | GTTTCAAGAC | 540 |
| GTGACTTTCA | CCATGGGTCA | GGTGGTGTCT | CGAGAAGGCC | AAGGAAGGCA | GGAGACTCTA | 600 |
| TTCCGATGTA | TAAGAAGTAT | GCCCTCCCAC | CCGGACCGGG | CCTACAACAG | CTGCTATAGC | 660 |
| GCAGGTGTCT | TCCATTTACA | CCAAGGGGAT | ATTCTGAGTG | TCATAATTCC | CCGGGCAAGG | 720 |
| GCGAAACTTA | ACCTCTCTCC | ACATGGAACC | TTCCTGGGGT | TTGTGAAACT | GTGATTGTGT | 780 |
| TATAAAAAGT | GGCTCCCAGC | TTGGAAGACC | AGGGTGGGTA | CATACTGGAG | ACAGCCAAGA | 840 |
| GCTGAGTATA | TAAAGGAGAG | GGAATGTGCA | GGAACAGAGG | CGTCTTCCTG | GGTTTGGCTC | 900 |
| CCCGTTCCTC | ACTTTTCCCT | TTTCATTCCC | ACCCCCTAGA | CTTTGATTTT | ACGGATATCT | 960 |
| TGCTTCTGTT | CCCCATGGAG | CTCCGAATTC | TTGCGTGTGT | GTAGATGAGG | GGCGGGGACG | 1020 |
| GGCGCCAGGC | ATTGTCCAGA | CCTGGTCGGG | CCCACTGGAA | GCATCCAGAA | CAGCACCACC | 1080 |
| ATCTAGCGGC | CGCTCGAGGG | AAGCACCCGC | CGGTTGGCCG | AAGTCCACGA | AGCCGCCCTC | 1140 |
| TGCTAGGGAA | AACCCCTGGT | TCTCCATGCC | ACACCTCTCT | CCAGGTGCCC | TCTGCCTCTT | 1200 |
| CACCCCACAA | GAAGCCTTAT | CCTACGTCCT | TCTCTCCATC | TATCGGACCC | CAGTTTCCAT | 1260 |
| CACTATCTCC | AGAGATGTAG | CTATTATGCG | CCCGTCTACA | GGGGGTGCCC | GACGATGACG | 1320 |
| GTGCCTTCGC | AGTCAAATTA | CTCTTCGGGT | CCCAAGGTTT | GGCTTTCACG | CGCTCCATTG | 1380 |
| CCCCGGCGTG | GCAGGCCATT | CCAAGCCCTT | CCGGGCTGGA | ACTGGTGTCG | GAGGAGCCTC | 1440 |
| GGGTGTATCG | TACGCCCTGG | TGTTGGTGTT | GCCTCACTCC | TCTGAGCTCT | TCTTTCTGAT | 1500 |
| CAAGCCCTGC | TTAAAGTTAA | ATAAAATAGA | ATGAATGATA | AAAAAAAAA | | 1550 |

(2) INFORMATION FOR SEQ ID NO:2:

(i) SEQUENCE CHARACTERISTICS:
(A) LENGTH: 234 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:2:

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

-continued

```
Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
 50                  55                  60

Leu Gln Gly Thr Gly Gly Pro Ser Gln Asn Gly Glu Gly Tyr Pro Trp
 65                  70                  75                  80

Gln Ser Leu Pro Glu Gln Ser Ser Asp Ala Leu Glu Ala Trp Glu Ser
                 85                  90                  95

Gly Glu Arg Ser Arg Lys Arg Ala Val Leu Thr Gln Lys Gln Lys
                100                 105                 110

Asn Asp Ser Asp Val Thr Glu Val Met Trp Gln Pro Ala Leu Arg Arg
        115                 120                 125

Gly Arg Gly Leu Gln Ala Gln Gly Tyr Gly Val Arg Ile Gln Asp Ala
130                 135                 140

Gly Val Tyr Leu Leu Tyr Ser Gln Val Leu Phe Gln Asp Val Thr Phe
145                 150                 155                 160

Thr Met Gly Gln Val Val Ser Arg Glu Gly Gln Gly Arg Gln Glu Thr
                165                 170                 175

Leu Phe Arg Cys Ile Arg Ser Met Pro Ser His Pro Asp Arg Ala Tyr
                180                 185                 190

Asn Ser Cys Tyr Ser Ala Gly Val Phe His Leu His Gln Gly Asp Ile
                195                 200                 205

Leu Ser Val Ile Ile Pro Arg Ala Arg Ala Lys Leu Asn Leu Ser Pro
210                 215                 220

His Gly Thr Phe Leu Gly Phe Val Lys Leu
225                 230

(2) INFORMATION FOR SEQ ID NO:3:

(i) SEQUENCE CHARACTERISTICS:
        (A) LENGTH: 1430 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

TTTTATTTCA GGTCCCGGAT CCGCGCTTGA AACCACAGCT GTTGGCAGGG TCCCCAGCTC    60

ATGCCAGCCT CATCTCCTTT CTTGCTAGCC CCCAAAGGGC CTCCAGGCAA CATGGGGGGC   120

CCAGTCAGAG AGCCGGCACT CTCAGTTGCC CTCTGGTTGA GTTGGGGGGC AGCTCTGGGG   180

GCCGTGGCTT GTGCCATGGC TCTGCTGACC CAACAAACAG AGCTGCAGAG CCTCAGGAGA   240

GAGGTGAGCC GGCTGCAGGG GACAGGAGGC CCCTCCCAGA ATGGGGAAGG GTATCCCTGG   300

CAGAGTCTCC CGGAGCAGAG TTCCGATGCC CTGGAAGCCT GGGAGAATGG GGAGAGATCC   360

CGGAAAAGGA GAGCAGTGCT CACCCAAAAA CAGAAGAAGC AGCACTCTGT CCTGCACCTG   420

GTTCCCATTA ACGCCACCTC CAAGGATGAC TCCGATGTGA CAGAGGTGAT GTGGCAACCA   480

GCTCTTAGGC GTGGGAGAGG CCTACAGGCC CAAGGATATG GTGTCCGAAT CCAGGATGCT   540

GGAGTTTATC TGCTGTATAG CCAGGTCCTG TTTCAAGACG TGACTTTCAC CATGGGTCAG   600

GTGGTGTCTC GAGAAGGCCA AGGAAGGCAG GAGACTCTAT TCCGATGTAT AAGAAGTATG   660

CCCTCCCACC CGGACCGGGC CTACAACAGC TGCTATAGCG CAGGTGTCTT CCATTTACAC   720

CAAGGGGATA TTCTGAGTGT CATAATTCCC CGGGCAAGGG CGAAACTTAA CCTCTCTCCA   780

CATGGAACCT TCCTGGGACT TTGATTTTAC GGATATCTTG CTTCTGTTCC CCATGGAGCT   840
```

-continued

```
CCGAATTCTT GCGTGTGTGT AGATGAGGGG CGGGGGACGG GCGCCAGGCA TTGTTCAGAC     900

CTGGTCGGGG CCCACTGGAA GCATCCAGAA CAGCACCACC ATCTAGCGGC CGCTCGAGGG     960

AAGCACCCGC CGGTTGGCCG AAGTCCACGA AGCCGCCCTC TGCTAGGGAA AACCCCTGGT    1020

TCTCCATGCC ACACCTCTCT CCAGGTGCCC TCTGCCTCTT CACCCCACAA GAAGCCTTAT    1080

CCTACGTCCT TCTCTCCATC TATCGGACCC CAGTTTCCAT CACTATCTCC AGAGATGTAG    1140

CTATTATGCG CCCGTCTACA GGGGTGCCC GACGATGACG GTGCCTTCGC AGTCAAATTA    1200

CTCTTCGGGT CCCAAGGTTT GGCTTTCACG CGCTCCATTG CCCCGGCGTG GCAGGCCATT    1260

CCAAGCCCTT CCGGGCTGGA ACTGGTGTCG GAGGAGCCTC GGGTGTATCG TACGCCCTGG    1320

TGTTGGTGTT GCCTCACTCC TCTGAGCTCT TCTTTCTGAT CAAGCCCTGC TTAAAGTTAA    1380

ATAAAATAGA ATGAATGATA AAAAAAAAAA AAAAAAAAA AAAAAAAAAA               1430
```

(2) INFORMATION FOR SEQ ID NO:4:

(i) SEQUENCE CHARACTERISTICS:
        (A) LENGTH: 247 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Pro Ala Ser Ser Pro Phe Leu Leu Ala Pro Lys Gly Pro Pro Gly
 1               5                  10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240
```

```
His Gly Thr Phe Leu Gly Leu
            245

(2) INFORMATION FOR SEQ ID NO:5:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Tyr Glu Pro Ile Tyr Leu Gly Gly Val Phe Gln Leu Glu Lys Gly Asp
1               5                   10                  15

Arg Leu Ser Ala Glu Ile Asn Arg
            20

(2) INFORMATION FOR SEQ ID NO:6:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Tyr Asn Xaa Cys Tyr Xaa Ala Gly Val Phe His Leu His Gln Gly Asp
1               5                   10                  15

Ile Leu Ser Val Ile Ile Pro Arg
            20

(2) INFORMATION FOR SEQ ID NO:7:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Val Pro Ser Glu Gly Leu Tyr Leu Ile Tyr Ser Gln Val Leu Phe Lys
1               5                   10                  15

(2) INFORMATION FOR SEQ ID NO:8:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Ile Gln Asp Ala Gly Val Tyr Leu Leu Tyr Arg Gln Val Leu Phe Gln
1               5                   10                  15

(2) INFORMATION FOR SEQ ID NO:9:

(i) SEQUENCE CHARACTERISTICS:
        (A) LENGTH: 233 amino acids
        (B) TYPE: amino acid
```

(C) STRANDEDNESS: single
(D) TOPOLOGY: linear (ii) MOLECULE TYPE: protein (xi) SEQUENCE DESCRIPTION: SEQ ID NO:9:

Met Ser Thr Glu Ser Met Ile Arg Asp Val Glu Leu Ala Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
50                      55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

(2) INFORMATION FOR SEQ ID NO:10:

(i) SEQUENCE CHARACTERISTICS:
        (A) LENGTH: 281 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Pro Pro Leu Pro
    50                  55                  60

Pro Leu Pro Leu Pro Pro Leu Lys Lys Arg Gly Asn His Ser Thr Gly
65                  70                  75                  80

```
Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280

(2) INFORMATION FOR SEQ ID NO:11:

(i) SEQUENCE CHARACTERISTICS:
        (A) LENGTH: 281 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140
```

```
Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
                260                 265                 270

Ser Phe Phe Gly Ala Phe Leu Val Gly
        275                 280
```

(2) INFORMATION FOR SEQ ID NO:12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

ATATGGATCC CAGCTCATGC CAGCCTCA                                              28

(2) INFORMATION FOR SEQ ID NO:13:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

AGTAAAGCTT GGAATTATGA CACTCAGAAT ATCCC                                  35

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

CAGCTCATGC CAGCCTCA                                                            18

(2) INFORMATION FOR SEQ ID NO:15:

(i) SEQUENCE CHARACTERISTICS:
        (A) LENGTH: 23 base pairs
        (B) TYPE: nucleic acid

```
            (C) STRANDEDNESS: single
            (D) TOPOLOGY: linear (ii) MOLECULE TYPE: cDNA (xi) SEQUENCE DESCRIPTION: SEQ ID NO:15:

TATCCGTAAA ATCAAAGTCC CAG                                              23

(2) INFORMATION FOR SEQ ID NO:16:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:16:

CATATGCACA GAGCTGCAGA GCCTCAGGAG                                       30

(2) INFORMATION FOR SEQ ID NO:17:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:17:

TCACAGTTTC ACAAACCCCA GGAAG                                            25

(2) INFORMATION FOR SEQ ID NO:18:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:18:

GTAAAATCAA AGTCCCAGGA AGGT                                             24
```

TNF-RELATED DEATH LIGAND

CROSS-REFERENCE TO RELATED APPLICATIONS

This application claims the benefit of the following provisional application: U.S. Serial No. 60/060,475, filed Sep. 30, 1997, under 35 USC 119(e)(i).

FIELD OF THE INVENTION

The invention relates to a novel tumor necrosis factor (TNF) homolog designated herein as TNF-related death ligand (TRDL).

BACKGROUND OF THE INVENTION

Tumor necrosis factor (TNF), named for its ability to shrink tumors, is made by cells of the immune system and is a member of an emerging family of cytokines with important roles in immune regulation, inflammation and cancer. The family includes seven members, in addition to TNF, which share limited sequence homology that is confined to the C-terminal portion of the molecules. With exception of TNF-β, each of these of ligands are type II membrane associated proteins that require cell surface presentation to elicit effects from corresponding target cells (Wiley, S. R., Schooley, K., Smolak, P. J., Din, W. S., Huang, C-P., Nicholl, J. K., Sutherland, G. R., Davis Smith, T., Rauch, C., Smith, C. A., and Goodwin, R. G. (1995) Identification and characterization of a new member of the TNF family that induces apoptosis. *Immunity.* 3, 673–682). This cytokine family interacts with a growing list of target transmembrane receptors with complicated signaling strategies and often contradictory biological effects (Wiley, S. R., Schooley, K., Smolak, P. J., Din, W. S., Huang, C-P., Nicholl, J. K., Sutherland, G. R., Davis Smith, T., Rauch, C., Smith, C. A., and Goodwin, R. G. (1995) Identification and characterization of a new member of the TNF family that induces apoptosis. *Immunity.* 3, 673–682).

The interaction of TNF-α with the TNFR-1 receptor typifies the biological diversity of the TNF ligand receptor family. Ligation of TNFR-1 can activate NF-κB and elicit an inflammatory response in a variety of cell types (Beg, A. A. and Baltimore, D. (1996) An essential role for NF-κB in preventing TNF-α-induced cell death. *Science.* 274, 782–784. Wang, C-Y., Mayo, M. W., and Baldwin, A. S. Jr. (1996) TNF-and cancer therapy-induced apoptosis: potentiation by inhibition of NF-κB. *Science.* 274, 784–787. VanAntwerp, D. J., Martin, S. J., Kafri, T., Green, D. R., and Verma, I. M. (1996) Suppression of TNF-α-induced apoptosis by NF-κB. *Science.* 274, 787–789).

Alternatively, TNFR-1 activation can also induce apoptosis (Pan, G., O'Rourke, K, Chinnaiyan, A. M., Gentz, R., Ebner, R., Ni, J., and Dixit, V. (1997) The receptor for the cytotoxic ligand TRAIL. *Science.* 276, 111–113). The mechanisms that regulate these two pathways and the final cellular outcome remain unclear, but offer interesting prospects for therapeutic intervention. The importance of this life death balance in human disease can be seen in the observation that TNF fails to efficiently kill many types of cancer cells (Wang, C-Y., Mayo, M. W., and Baldwin, A. S. Jr. (1996) TNF-and cancer therapy-induced apoptosis: potentiation by inhibition of NF-κB. *Science.* 274, 784–787. Baichwal, V. R., and Baeuerle, P. A. (1997) Apoptosis: Activate NF-κB or die? *Current Biology.* 7, R94–R96). Recent evidence suggests that TNF undermines its own killing powers by activating NF-κB, a key molecule that can block the apoptosis pathway (Beg, A. A. and Baltimore, D. (1996) An essential role for NF-κB in preventing TNF-α-induced cell death. *Science.* 274, 782–784. Wang, C-Y., Mayo, M. W., and Baldwin, A. S. Jr. (1996) TNF-and cancer therapy-induced apoptosis: potentiation by inhibition of NF-κB. *Science.* 274, 784–787. VanAntwerp, D. J., Martin, S. J., Kafri, T., Green, D. R., and Verma, I. M. (1996) Suppression of TNF-α-induced apoptosis by NF-κB. *Science.* 274, 787–789. Liu, Z-G., Hsu, H., Goeddel, D., and Karin, M. (1996) Dissection of the TNF receptor 1 effector functions: JNK activation is not linked to apoptosis while NF-κB activation prevents cell death. *Cell.* 87, 565–576. Wu, M., Lee, H., Bellas, R. E., Schauer, S. L., Arsura, M., Katz, D., FitzGerald, M. J., Rothstein, T. L., Sherr, D. H., and Sonenshein, G. E. (1996) Inhibition of NF-κB/Rel induces apoptosis of murine B cells. *EMBO J.* 15, 4682–4690). This blockade may render tumor cells resistant to immune surveillance and confound chemotherapeutic approaches that rely on tumor cell apoptosis. Disruption of this protective mechanism may, therefore, sensitize cells to TNF mediated killing (Beg, A. A. and Baltimore, D. (1996) An essential role for NF-κB in preventing TNF-α-induced cell death. *Science.* 274, 782–784. Wang, C-Y., Mayo, M. W., and Baldwin, A. S. Jr. (1996) TNF-and cancer therapy-induced apoptosis: potentiation by inhibition of NF-κB. *Science.* 274, 784–787. VanAntwerp, D. J., Martin, S. J., Kafri, T., Green, D. R., and Verma, I. M. (1996) Suppression of TNF-α-induced apoptosis by NF-κB. *Science.* 274, 787–789).

Recent advances in the understanding of TNF signaling have elucidated discrete molecular targets for potential blockade of NF-κB activation and apoptosis in cells responding to TNF (Beg, A. A. and Baltimore, D. (1996) An essential role for NF-κB in preventing TNF-α-induced cell death. *Science.* 274, 782–784. Wang, C-Y., Mayo, M. W., and Baldwin, A. S. Jr. (1996) TNF-and cancer therapy-induced apoptosis: potentiation by inhibition of NF-κB. *Science.* 274, 784–787. VanAntwerp, D. J., Martin, S. J., Kafri, T., Green, D. R., and Verma, I. M. (1996) Suppression of TNF-α-induced apoptosis by NF-κB. *Science.* 274, 787–789. Wu, M., Lee, H., Bellas, R. E., Schauer, S. L., Arsura, M., Katz, D., FitzGerald, M. J., Rothstein, T. L., Sherr, D. H., and Sonenshein, G. E. (1996) Inhibition of NF-κB/Rel induces apoptosis of murine B cells. *EMBO J.* 15, 4682–4690). These responses are facilitated by the recruitment of signaling proteins to activated TNF receptors. Some of these signaling proteins, including TRADD (TNFR1-associated death domain protein), TRAF2 (TNFR-associated protein-2) and RIP (receptor interacting protein kinase) appear to initiate activation of NF-κB. Chinnaiyan, A. M., O'Rourke, K, Yu, G-L., Lyons, R. H., Garg, M., Duan, D. R., Xing, L., Gentz, R., Ni, J., and Dixit, V. M. (1996) Signal transduction by DR3, a death domain-containing receptor related to TNFR-1 and CD95. *Science.* 274, 990–992. Recruitment of other proteins, including FADD (Fas-associated death domain protein) and FLICK (FADD-like interleukin converting enzyme) induces apoptosis (Boldin, M. P., Goncharov, T. M., Goltsev, Y. V., and Wallach, D. (1996) Involvement of MACH, a novel MORT1/FADD-interacting protease, in Fas/APO-1-and TNF receptor-induced cell death. *Cell.* 85, 803–815. Muzio, M., Chinnaiyan, A. M., Kischkel, F. C., O'Rourke, K., Shevchenko, A., Ni, J., Scaffidi, C., Bretz, J. D., Zhang, M., Gentz, R., Mann, M., Krammer, P. H., Peter, M. E., and Dixit, V. (1996) FLICE, a novel FADD-homologous ICE/CED-3-like protease, is recruited to the CD95 (Fas/APO-1) death-inducing signaling complex. *Cell.* 85, 817–827).

This emerging biology has created considerable interest among researchers for potential therapeutic intervention, particularly in cancer, inflammatory diseases, and neurodegenerative disorders. Thus, it will be clear to the skilled artisan that there is a continuing need for novel members of the TNF family of inflammatory cytokines involved in apoptosis and NF-κB activation.

INFORMATION DISCLOSURE

Wiley et al., *Immunity* 3, 673–682 (1995).
Beg, A. A. and D. Baltimore, *Science* 274, 782–784 (1996).
Wang et al., *Science* 274, 784–787 (1996).
VanAntwerp et al., *Science* 274, 787–789 (1996).
Pan et al., *Science* 276, 111–113 (1997).
Baichwal et al., *Current Biology* 7, R94–R96 (1997).
Liu et al., *Cell* 87, 565–576 (1996).
Wu et al., *EMBO J* 15, 4682–4690 (1996).
Chinnaiyan et al., *Science* 274, 990–992 (1996).
Boldin et al., *Cell* 85, 803–815 (1996).
Muzio et al., *Cell* 85, 817–827 (1996).
Altschul et al., *J. Mol. Bio.* 215, 403–410 (1990).
Idziorek et al., *J. Immuno. Meth.* 185:249–258 (1995).
X. M. Wang, et al., *Human Immunol* 37: 264 (1993).

SUMMARY OF THE INVENTION

The present invention provides isolated nucleic acid molecules comprising a polynucleotide encoding a novel TNF homolog designated herein as TRDL, or a fragment thereof. TRDL polypeptides of the invention include two alternative splice variants of TRDL, designated herein as TRDL-11 and TRDL-14, which have the amino acid sequences shown in FIGS. 3 and 4 (SEQ ID NO:2 and SEQ ID NO:4, respectively). Preferred fragments of TRDL include the extracellular portion of TRDL-11 and of TRDL-14.

In a preferred embodiment, the nucleic acid molecules comprise a polynucleotide having the nucleotide sequence of SEQ ID NO:1 or SEQ ID NO:3. In another aspect, the invention provides an isolated nucleic acid molecule comprising a polynucleotide which hybridizes under stringent conditions to a polynucleotide encoding TRDL-11 or TRDL-14, or fragments thereof.

The present invention also provides vectors comprising the isolated nucleic acid molecules of the invention, host cells into which such vectors have been introduced, and recombinant methods of obtaining a TRDL polypeptide comprising culturing the above-described host cell and isolating the TRDL polypeptide.

In another aspect, the invention provides isolated TRDL polypeptides, as well as fragments thereof. In a preferred embodiment, the TRDL polypeptides have the amino acid sequence of SEQ ID NO:2 or SEQ ID NO:4. Isolated antibodies, both polyclonal and monoclonal, that bind specifically to TRDL polypeptides are also provided.

The invention also provides a method for the identification of cells having a high affinity receptor for TRDL, the method comprising:
 (a) labeling an isolated TRDL polypeptide
 (b) contacting the labeled TRDL polypeptide obtained in step (a) with cells of a mammalian cell line;
 (c) washing the cells obtained in step (b) to remove unbound TRDL; and
 (d) determining the presence of the labeled TRDL polypeptide in the washed cells obtained in step (c);
whereby the presence of labeled TRDL polypeptide in the washed cells obtained in step (c) indicates the presence of a high affinity receptor for TRDL on the cells.

In another embodiment, the invention relates to a method for the identification of an agent which inhibits the binding of TRDL to its receptor, the method comprising:
 (a) labeling an isolated TRDL polypeptide;
 (b) contacting the labeled TRDL polypeptide obtained in step (a)
  with cells of a mammalian cell line
  (i) in the presence of a test agent; and
  (ii) in the absence of a test agent;
 (c) washing the cells
  (i) obtained in step (b)(i); and
  (ii) obtained in step (b)(ii) to remove unbound TRDL;
 (d) determining the amount of labeled TRDL polypeptide in
  (i) the washed cells obtained in step (c)(i); and
  (ii) the washed cells obtained in step (c)(ii); and
 (e) comparing the amount of labeled TRDL polypeptide determined in step (d)(i) to that determined in (d)(ii);
whereby a lower amount of labeled TRDL polypeptide in sample (d)(i) than in sample (d)(ii) indicates that said agent inhibited the binding of TRDL to its receptor.

In another embodiment, the invention relates to a method for the identification of an agent which enhances the binding of TRDL to its receptor, the method comprising:
 (a) labeling an isolated TRDL polypeptide;
 (b) contacting the labeled TRDL polypeptide obtained in step (a)
  with cells of a mammalian cell line
  (i) in the presence of a test agent; and
  (ii) in the absence of a test agent;
 (c) washing the cells
  (i) obtained in step (b)(i); and
  (ii) obtained in step (b)(ii) to remove unbound TRDL;
 (d) determining the amount of labeled TRDL polypeptide in
  (i) the washed cells obtained in step (c)(i); and
  (ii) the washed cells obtained in step (c)(ii); and
 (e) comparing the amount of labeled TRDL polypeptide determined in step (d)(i) to that determined in (d)(ii);
whereby a higher amount of labeled TRDL polypeptide in sample (d)(i) than in sample (d)(ii) indicates that said agent has enhanced the binding of TRDL to its receptor.

In another embodiment, the invention provides A method for the identification of a cell line that undergoes apoptosis upon interaction with TRDL, the method comprising:
 (a) dividing the cells of a culture of a mammalian cell line into a test culture and a control culture;
 (b) contacting a TRDL polypeptide with the test culture of step (a);
 (c) determining the quantity of cells of
  (i) the test culture obtained in step (b); and
  (ii) the control culture of step (a);
   that have undergone apoptosis; and
 (d) comparing the quantity of cells determined to have undergone apoptosis in the test culture of step (c)(i) with the quantity of cells determined to have undergone apoptosis in the control culture of step (c)(ii);
whereby a determination that the quantity of cells having undergone apoptosis in said test culture is higher than in said control culture indicates that said mammalian cell line undergoes apoptosis upon interaction with TRDL.

In yet another embodiment, the invention provides a method for the identification of an agent capable of inhibiting TRDL-mediated induction of apoptosis, said method comprising (a) determining the quantity of cells that have undergone apoptosis in a test culture and a control culture, wherein said test culture comprises mammalian cells capable of undergoing apoptosis upon interaction with TRDL which have been contacted with a TRDL polypeptide in the presence of a test agent, and said control culture comprises mammalian cells capable of undergoing apoptosis upon interaction with TRDL which have been contacted with a TRDL polypeptide in the absence of a test agent; and (b) comparing the quantity of cells determined to have undergone apoptosis in the test culture of step (a) with the quantity of cells determined to have undergone apoptosis in the control culture of step (a);

whereby a determination that the quantity of cells having undergone apoptosis in said test culture is lower than in said control culture indicates that said test agent inhibits TRDL-mediated induction of apoptosis.

In yet another embodiment, the invention provides a method for the identification of an agent capable of enhancing TRDL-mediated induction of apoptosis, said method comprising (a) determining the quantity of cells that have undergone apoptosis in a test culture and a control culture, wherein said test culture comprises mammalian cells capable of undergoing apoptosis upon interaction with TRDL which have been contacted with a TRDL polypeptide in the presence of a test agent, and said control culture comprises mammalian cells capable of undergoing apoptosis upon interaction with TRDL which have been contacted with a TRDL polypeptide in the absence of a test agent; and (b) comparing the quantity of cells determined to have undergone apoptosis in the test culture of step (a) with the quantity of cells determined to have undergone apoptosis in the control culture of step (a);

whereby a determination that the quantity of cells having undergone apoptosis in said test culture is higher than in said control culture indicates that said test agent enhances TRDL-mediated induction of apoptosis.

In yet another embodiment, the invention provides a method for the identification of an agent capable of inhibiting TRDL-mediated prevention of apoptosis, said method comprising:

(a) determining the quantity of cells that have undergone apoptosis in a test culture and a control culture, wherein said test culture comprises mammalian cells that are prevented from undergoing apoptosis upon interaction with TRDL which have been contacted with a TRDL polypeptide in the presence of a test agent, and said control culture comprises mammalian cells that are prevented from undergoing apoptosis upon interaction with TRDL which have been contacted with a TRDL polypeptide in the absence of a test agent; and (b) comparing the quantity of cells determined to have undergone apoptosis in the test culture of step (a) with the quantity of cells determined to have undergone apoptosis in the control culture of step (a);

whereby a determination that the quantity of cells having undergone apoptosis in said test culture is higher than in said control culture indicates that said test agent inhibits TRDL-mediated prevention of apoptosis.

In yet another embodiment, the invention provides a method for the identification of an agent capable of enhancing TRDL-mediated prevention of apoptosis, said method comprising (a) determining the quantity of cells that have undergone apoptosis in a test culture and a control culture, wherein said test culture comprises mammalian cells that are prevented from undergoing apoptosis upon interaction with TRDL which have been contacted with a TRDL polypeptide in the presence of a test agent, and said control culture comprises mammalian cells that are prevented from undergoing apoptosis upon interaction with TRDL which have been contacted with a TRDL polypeptide in the absence of a test agent; and (b) comparing the quantity of cells determined to have undergone apoptosis in the test culture of step (a) with the quantity of cells determined to have undergone apoptosis in the control culture of step (a);

whereby a determination that the quantity of cells having undergone apoptosis in said test culture is lower than in said control culture indicates that said test agent enhances TRDL-mediated prevention of apoptosis.

BRIEF DESCRIPTION OF THE FIGURES

FIGS. 1A and 1B. FIGS. 1A and 1B are sequence comparisons showing the results of an Incyte LifeSeq database search for TNF homologs. The database was searched using the basic local alignment tool (BLAST) and the sequence for TNF-α (accession #M10988). Two regions in the coding region of clone 78258 have interesting regions of homology with TNF-α. FIG. 1A shows one such region of homology: a region of clone 78258 (SEQ ID NO:5) is compared to a region of TNF-α (SEQ ID NO:6). FIG. 1B shows another region of homology: a second region of clone 78258 (SEQ ID NO:7) is compared to a second region of TNF-α (SEQ ID NO:8).

FIG. 2 shows cluster assembly and consensus of clones within a 709 bp cDNA sequence. A contiguous 709 bp cDNA sequence was obtained using the LifeSeq Assembly function for the clones in cluster 99092, including clone 78258. Included in the sequence is clone 798247, which lies furthest upstream in the contig.

FIG. 3. FIG. 3 shows the nucleotide sequence (SEQ ID NO:1) and predicted amino acid sequence (SEQ ID NO:2) of TRDL-11.

FIG. 4. FIG. 4 shows the nucleotide sequence (SEQ ID NO:3) and predicted amino acid sequence (SEQ ID NO:4) of TRDL-14.

FIG. 5. FIG. 5 shows a DNA sequence alignment of the nucleotide sequences of clones TRDL-11 (SEQ ID NO:1) and TRDL-14 (SEQ ID NO:3). Clones 11 & 14 are nearly identical with the exception of a 48 base pair stretch present in clone 14 which is missing from clone 11, and 183 base pairs 5 present at the 3' end of clone 11 which are absent in clone 14.

FIG. 6. FIG. 6 shows an alignment of the predicted amino acid sequences encoded by clones TRDL-11 (SEQ ID NO:2) and TRDL-14 (SEQ ID NO:4), to the amino acid sequences of TNF family members TNF-α (SEQ ID NO:9), FasL (SEQ ID NO:10), and TRAIL (SEQ ID NO:11). Regions of homology are highlighted in gray.

FIG. 7. FIG. 7 shows the results of electronic northern blots for clones 177393 and 798247. These 2 clones are representative members of the clusters which encompass the sequence for TRDL-11 (SEQ ID NO:1) and TRDL-14 (SEQ ID NO:3). They are expressed mainly in inflammatory tissues and tissues with an abundant peripheral blood supply.

FIG. 8A is a northern blot showing the tissue distribution of expression of clone 798247. A multiple tissue Northern analysis was carried out using full-length 798247 as the probe. Two separate blots representing the indicated tissues (1=heart, 2=brain, 3=placenta, 4=lung, 5=liver, 6=skeletal muscle, 7=kidney, 8=pancreas, 9=spleen, 10=thymus, 11=prostate, 12=testis, 13=ovary, 14=small intestine, 15=colon, 16=peripheral blood leukocytes) were analyzed in parallel. The probe hybridized to messages at approximately 1.6 & 1.8 kb. Signals were quantified using a phosphoimager, and are displayed in the plot as relative phosphorescence. FIG. 8B is a graph showing the relative phosphorescence of the labeled 798247 probe in northern blots from the indicated tissue type.

FIG. 9A is a northern blot showing the distribution of TRDL-14 expression in human cancer cell lines. A multiple cancer cell line Northern analysis (1=HL-60, 2=HeLaS3, 3=K-562, 4=MOLT-4, 5=BL Raji, 6=SW480, 7=A549, and 8=G361) was carried out using the coding region of TRDL-14 as the probe. The probe hybridized to messages at approx. 1.7 kb (bars 1 & 2) and 2.5 kb (bars 3& 4) in HeLa and SW480 cells. A third mRNA species at 4.4 kb was moderately expressed in HeLa, SW480, HL-60, and K-562 cells, and at low levels in MOLT-4, BL Raji, A549, and G351 cells (bars 5–12). FIG. 9B is a graph showing the relative phosphorescence of the labeled 798247 probe in northern blots from the indicated cancer cell line.

FIG. 10A is a graph showing the distribution of TRDL-14 expression in normal tumor tissue samples. High levels of expression were seen in tumor samples from duodenum & colon. Expression in lung was high in both normal and tumor samples. FIG. 10B is a graph showing the distribution of TRDL-14 expression in normal and tumor tissue samples. A high level of expression was seen in the tumor sample from pancreas. Expression was higher in normal than tumor samples from gallbladder, thymus, adrenal, breast, and thyroid.

DETAILED DESCRIPTION

Figure 2:
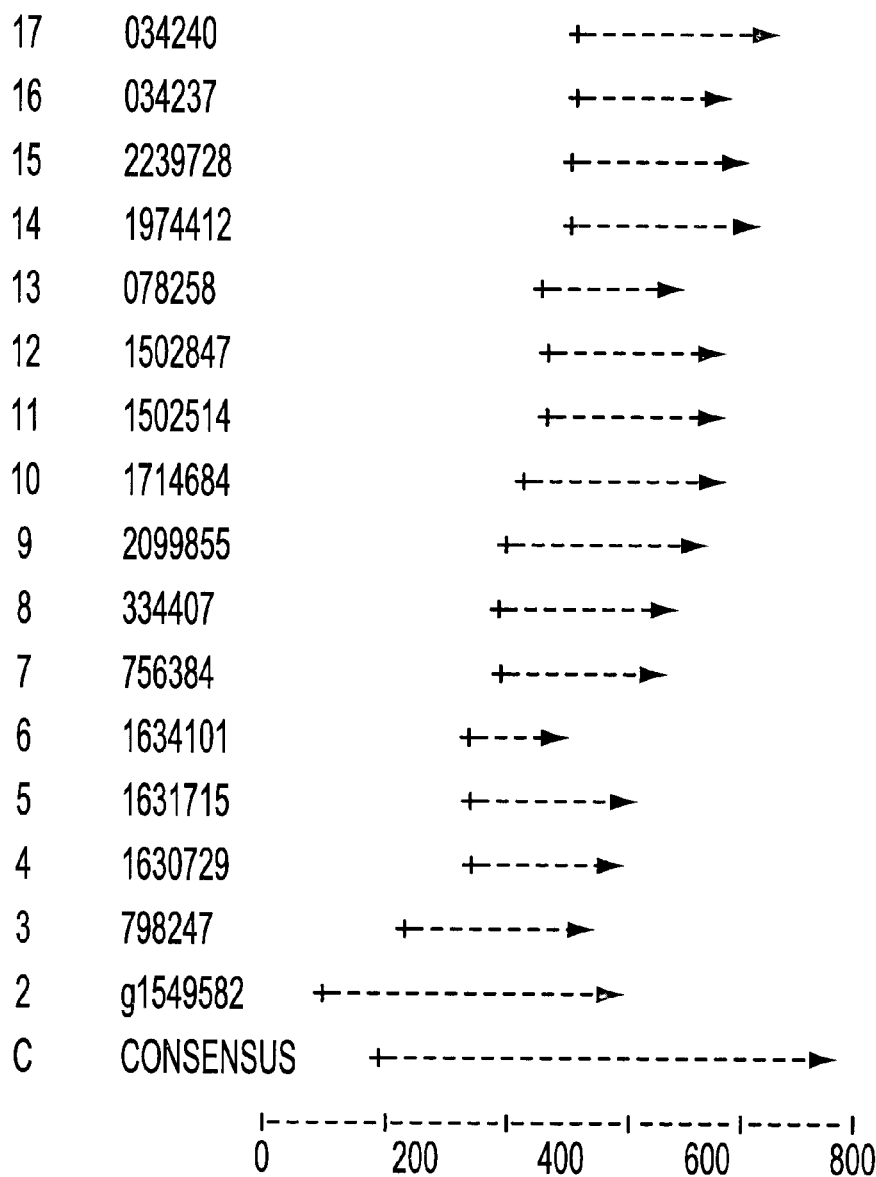
FIG. 2.

The present invention provides isolated nucleic acid molecules comprising polynucleotides encoding two alternative splice variants of the TRDL polypeptide, designated herein as TRDL-11 and TRDL-14, and having the amino acid sequence shown in FIGS. 4 and 5 (SEQ ID NO:2 and SEQ ID NO:4, respectively). Unless otherwise indicated, all references to TRDL are to be understood as referring to either TRDL-11 or TRDL-14.

The TRDL polypeptides of the present invention share sequence homology with the family of cytokines which includes TNF-α, FasL, and TRAIL. Sequence conservation with molecules like TNF, TRAIL and FasL is confined primarily to two, short stretches within 100 amino acids from the carboxy terminus. The overall percent identity of the C-terminal domain of TRDL to TNFα, FasL and TRAIL is 17%, 17% and 12%, respectively. Although not striking, this level of homology is typical of the TNF cytokine family. By comparison, TRAIL is only 28% homologous to FasL, 23% homologous to TNFα and 22% homologous to lymphotoxin β. Like these family members, TRDL contains a putative transmembrane segment near the N-terminus that is likely required for proper presentation of this molecule on cell surfaces. Wiley, S. R., Schooley, K, Smolak, P. J., Din, W. S., Huang, C-P., Nicholl, J. K, Sutherland, G. R., Davis Smith, T., Rauch, C., Smith, C. A., and Goodwin, R. G. (1995) Identification and characterization of a new member of the TNF family that induces apoptosis. *Immunity.* 3, 673–682.

Structural domains of the TRDL polypeptides of the present invention have been predicted via the Transmem program (Pharmacia & Upjohn, Kalamazoo, Mich.). Thus, the structural domains of TRDL-11, whose amino acid sequence is given in SEQ ID NO:2, are predicted to comprise an N-terminal cytoplasmic domain corresponding to amino acid residue 1 to about amino acid residue 23, a transmembrane region corresponding to about amino acid residue 24 to about amino acid residue 52, and a C-terminal extracellular domain corresponding to about amino acid residue 53 to about amino acid residue 2. The structural domains of TRDL-14, whose amino acid sequence is given in SEQ ID NO:4, are predicted to comprise an N-terminal cytoplasmic domain corresponding to amino acid residue 1 to about amino acid residue 23, a transmembrane region corresponding to about amino acid residue 24 to about amino acid residue 52, and a C-terminal extracellular domain corresponding to about amino acid residue 53 to about amino acid residue 247. The invention thus also provides nucleic acid molecules which encode the intracellular, transmembrane, or extracellular region of either TRDL-11 or TRDL-14.

As will be understood by the skilled artisan, the transmembrane region of each TRDL polypeptide described above is identified in accordance with conventional criteria for identifying that type of hydrophobic domain. Of course, the exact boundaries of the transmembrane region may vary slightly from those given above. Thus, the N-terminal boundary of the transmembrane domain of TRDL may begin 5 amino acid residues N-terminal to or C-terminal to the designated boundary, and the C-terminal boundary of the transmembrane domain of TRDL may begin 5 amino acid residues N-terminal to or C-terminal to the designated boundary. Of course, where the actual boundaries of the transmembrane region are shifted as described above, corresponding shifts in the C-terminal boundary of the intracellular domain and the N-terminal boundary of the extracellular domain will also be found.

The nucleotide sequences given in SEQ ID NO:1 and SEQ ID NO:3 correspond to the nucleotide sequences encoding TRDL-11 and TRDL-14, respectively. The isolation and sequencing of DNA encoding TRDL is described below at Example 1. The DNA of SEQ ID NO:1 (encoding TRDL-11), as compared to the DNA of SEQ ID NO:3 (encoding TRDL-14), contains an in-frame deletion of about 48 base pairs that encodes about 16 amino acids (about residue 111 to about residue 127 of TRDL-14) from the DNA of SEQ ID NO:3 (TRDL-14). The DNA of SEQ ID NO:3 (encoding TRDL-14), as compared to the DNA of SEQ ID NO:1 (encoding TRDL-11), lacks about 183 base pairs near the termination codon from the DNA of SEQ ID NO:1 (TRDL-11) (see FIG. 5).

As is described in Example 1, automated sequencing methods were used to obtain the nucleotide sequence of TRDL. The TRDL nucleotide sequences of the present invention were obtained for both DNA strands, and are believed to be 100% accurate. However, as is known in the art, nucleotide sequence obtained by such automated methods may contain some errors. Nucleotide sequences determined by automation are typically at least about 90%, more typically at least about 95% to at least about 99.9% identical to the actual nucleotide sequence of a given nucleic acid molecule. The actual sequence may be more precisely determined using manual sequencing methods, which are well known in the art. As is known in the art, an error in sequence which results in an insertion or deletion of one or more nucleotides may result in a frame shift in translation such that the predicted amino acid sequence will differ from that which would be predicted from the actual nucleotide sequence of the nucleic acid molecule, starting at the point of the mutation.

The TRDL DNA of the present invention includes cDNA, chemically synthesized DNA, DNA isolated by PCR, genomic DNA, and combinations thereof. Genomic TRDL DNA may be obtained by screening a genomic library with the TRDL cDNA described herein (See Example 3, section (e)). RNA transcribed from TRDL DNA is also encompassed by the present invention.

Due to the degeneracy of the genetic code, two DNA sequences may differ and yet encode identical amino acid sequences. The present invention thus provides isolated nucleic acid molecules having a polynucleotide sequence encoding any of the TRDL polypeptides of the invention, wherein said polynucleotide sequence encodes a TRDL polypeptide having the complete amino acid sequence of SEQ ID NO:2 or SEQ ID NO: 4, or fragments thereof.

Also provided herein are purified TRDL polypeptides, both recombinant and non-recombinant. Variants and derivatives of native TRDL proteins that retain any of the biological activities of TRDL are also within the scope of the present invention. One biological activity of TRDL is the ability to induce apoptosis. Assay procedures for detecting apoptosis of target cells are well known. These include the DNA laddering apoptosis assay and cell lysis assays described by Wiley et al. (WO 97/01633).

TRDL variants may be obtained by mutation of native TRDL-encoding nucleotide sequences, for example. A TRDL variant, as referred to herein, is a polypeptide substantially homologous to a native TRDL but which has an amino acid sequence different from that of native TRDL because of one or more deletions, insertions, or substitutions in the amino acid sequence. The variant amino acid or nucleotide sequence is preferably at least about 80% identical, more preferably at least about 90% identical, and most preferably at least about 95% identical, to a native TRDL sequence. The percentage of sequence identity, also termed homology, between a native and a variant TRDL sequence may be determined, for example, by comparing the two sequences using any of the computer programs commonly employed for this purpose, such as the Bestfit program (Wisconsin Sequence Analysis Package, Version 8 for Unix, Genetics Computer Group, University Research Park, Madison Wis.), which uses the algorithm of Smith and Waterman (*Adv. Appl. Math.* 2: 482–489 (1981)).

Alterations of the native amino acid sequence may be accomplished by any of a number of known techniques. For example, mutations may be introduced at particular locations by procedures well known to the skilled artisan, such as oligonucleotide-directed mutagenesis, which is described by Walder et al. (*Gene* 42:133 (1986)); Bauer et al. (*Gene* 37:73 (1985)); Craik (*BioTechniques,* January 1985, pp. 12–19); Smith et al. (*Genetic Engineering: Principles and Methods,* Plenum Press (1981)); and U.S. Pat. Nos. 4,518, 584 and 4,737,462.

TRDL variants within the scope of the invention may comprise conservatively substituted sequences, meaning that one or more amino acid residues of a TRDL polypeptide are replaced by different residues that do not alter the secondary and/or tertiary structure of the TRDL polypeptide. Such substitutions may include the replacement of an amino acid by a residue having similar physicochemical properties, such as substituting one aliphatic residue (Ile, Val, Leu or Ala) for another, or substitution between basic residues Lys and Arg, acidic residues Glu and Asp, amide residues Gln and Asn, hydroxyl residues Ser and Tyr, or aromatic residues Phe and Tyr. Further information regarding making phenotypically silent amino acid exchanges may be found in Bowie et al., *Science* 247:1306–1310 (1990). Other TRDL variants which might retain substantially the biological activities of TRDL are those where amino acid substitutions have been made in areas outside functional regions of the protein, for example, in a region falling outside of a receptor binding site.

In another aspect, the invention provides an isolated nucleic acid molecule comprising a polynucleotide which hybridizes under stringent conditions to a portion of the nucleic acid molecules described above, e.g. to at least about 15 nucleotides, preferably to at least about 20 nucleotides, more preferably to at least about 30 nucleotides, and still more preferably to at least about from 30 to at least about 100 nucleotides, of one of the previously described nucleic acid molecules. Such portions of nucleic acid molecules having the described lengths refer to, e.g., at least about 15 contiguous nucleotides of the reference nucleic acid molecule. By stringent hybridization conditions is intended overnight incubation at about 42° C. for about 2.5 hours in 6×SSC/0.1% SDS, followed by washing of the filters in 1.0×SSC at 65° C., 0.1% SDS.

Fragments of the TRDL-encoding nucleic acid molecules described herein, as well as polynucleotides capable of hybridizing to such nucleic acid molecules (including the fragments which encode the intracellular, transmembrane, or extracellular region of any of TRDL-1, TRDL-11, and TRDL-14) may be used as a probe or as primers in a polymerase chain reaction (PCR). Such probes may be used, e.g., to detect the presence of TRDL nucleic acids in in vitro assays, as well as in Southern and northern blots. Cell types expressing TRDL may also be identified by the use of such probes. Such procedures are well known, and the skilled artisan will be able to choose a probe of a length suitable to the particular application. For PCR, 5' and 3' primers corresponding to the termini of a desired TRDL nucleic acid molecule are employed to isolate and amplify that sequence using conventional techniques.

Other useful fragments of the TRDL nucleic acid molecules are antisense or sense oligonucleotides comprising a single-stranded nucleic acid sequence capable of binding to a target TRDL mRNA (using a sense strand), or TRDL DNA (using an antisense strand) sequence.

In another aspect, the invention includes TRDL polypeptides with or without associated native pattern glycosylation. TRDL expressed in yeast or mammalian expression systems (discussed below) may be similar to or significantly different from a native TRDL polypeptide in molecular weight and glycosylation pattern. Expression of TRDL in bacterial expression systems will provide non-glycosylated TRDL.

The polypeptides of the present invention are preferably provided in an isolated form, and preferably are substantially purified. TRDL polypeptides may be recovered and purified from recombinant cell cultures by well-known methods, including ammonium sulfate or ethanol precipitation, anion or cation exchange chromatography, phosphocellulose chromatography, hydrophobic interaction chromatography, affinity chromatography, hydroxylapatite chromatography and lectin chromatography. In a preferred embodiment, high performance liquid chromatography (HPLC) is employed for purification.

The present invention also relates to vectors comprising the polynucleotide molecules of the invention, as well as host cell transformed with such vectors. Any of the polynucleotide molecules of the invention may be joined to a vector, which generally includes a selectable marker and an origin of replication, for propagation in a host. Because the invention also provides TRDL polypeptides expressed from the polynucleotide molecules described above, vectors for the expression of TRDL are preferred. The vectors include DNA encoding any of the TRDL polypeptides described above or below, operably linked to suitable transcriptional or translational regulatory sequences, such as those derived from a mammalian, microbial, viral, or insect gene. Examples of regulatory sequences include transcriptional promoters, operators, or enhancers, mRNA ribosomal binding sites, and appropriate sequences which control transcription and translation. Nucleotide sequences are operably linked when the regulatory sequence functionally relates to the DNA encoding TRDL. Thus, a promoter nucleotide sequence is operably linked to a TRDL DNA sequence if the promoter nucleotide sequence directs the transcription of the TRDL sequence.

Selection of suitable vectors to be used for the cloning of polynucleotide molecules encoding TRDL, or for the expression of TRDL polypeptides, will of course depend upon the host cell in which the vector will be transformed, and, where applicable, the host cell from which the TRDL polypeptide is to be expressed. Suitable host cells for expression of TRDL polypeptides include prokaryotes, yeast, and higher eukaryotic cells, each of which is discussed below.

The TRDL polypeptides to be expressed in such host cells may also be fusion proteins which include regions from heterologous proteins. Such regions may be included to allow, e.g., secretion, improved stability, or facilitated purification of the polypeptide. For example, a sequence encoding an appropriate signal peptide can be incorporated into expression vectors. A DNA sequence for a signal peptide (secretory leader) may be fused in-frame to the TRDL sequence so that TRDL is translated as a fusion protein comprising the signal peptide. A signal peptide that is functional in the intended host cell promotes extracellular secretion of the TRDL polypeptide. Preferably, the signal sequence will be cleaved from the TRDL polypeptide upon secretion of TRDL from the cell. Non-limiting examples of signal sequences that can be used in practicing the invention include the yeast $\alpha$-factor and the honeybee melatin leader in sf9 insect cells.

In a preferred embodiment, the TRDL polypeptide will be a fusion protein which includes a heterologous region used to facilitate purification of the polypeptide. Many of the available peptides used for such a function allow selective binding of the fusion protein to a binding partner. For example, the TRDL polypeptide may be modified to comprise a peptide to form a fusion protein which specifically binds to a binding partner, or peptide tag. Non-limiting examples of such peptide tags include the 6-His tag, thioredoxin tag, hemaglutinin tag, GST tag, and OmpA signal sequence tag. As will be understood by one of skill in the art, the binding partner which recognizes and binds to the peptide may be any molecule or compound including metal ions (e.g., metal affinity columns), antibodies, or fragments thereof, and any protein or peptide which binds the peptide, such as the FLAG tag.

Suitable host cells for expression of TRDL polypeptides include prokaryotes, yeast, and higher eukaryotic cells. Suitable prokaryotic hosts to be used for the expression of TRDL include bacteria of the genera Escherichia, Bacillus, and Salmonella, as well as members of the genera Pseudomonas, Streptomyces, and Staphylococcus. For expression in, e.g., E. coli, a TRDL polypeptide may include an N-terminal methionine residue to facilitate expression of the recombinant polypeptide in a prokaryotic host. The N-terminal Met may optionally then be cleaved from the expressed TRDL polypeptide.

Expression vectors for use in prokaryotic hosts generally comprise one or more phenotypic selectable marker genes. Such genes generally encode, e.g., a protein that confers antibiotic resistance or that supplies an auxotrophic requirement. A wide variety of such vectors are readily available from commercial sources. Examples include pSPORT vectors, pGEM vectors (Promega), pPROEX vectors (LTI, Bethesda, Md.), Bluescript vectors (Stratagene), and pQE vectors (Qiagen).

TRDL may also be expressed in yeast host cells from genera including Saccharomyces, Pichia, and Kluveromyces. Preferred yeast hosts are S. cerevisiae and P. pastoris. Yeast vectors will often contain an origin of replication sequence from a $2\mu$ yeast plasmid, an autonomously replicating sequence (ARS), a promoter region, sequences for polyadenylation, sequences for transcription termination, and a selectable marker gene. Vectors replicable in both yeast and E. coli (termed shuttle vectors) may also be used. In addition to the above-mentioned features of yeast vectors, a shuttle vector will also include sequences for replication and selection in E. coli. Direct secretion of TRDL polypeptides expressed in yeast hosts may be accomplished by the inclusion of nucleotide sequence encoding the yeast a:-factor leader sequence at the 5' end of the TRDL-encoding nucleotide sequence.

Insect host cell culture systems may also be used for the expression of TRDL polypeptides. Expression of a TRDL polypeptide in baculovirus is described below in Example 4. Further information regarding the use of baculovirus systems for the expression of heterologous proteins in insect cells are reviewed by Luckow and Summers, *Bio/Technology* 6:47 (1988).

In a preferred embodiment, TRDL polypeptides are expressed in mammalian host cells. Non-limiting examples of suitable mammalian cell lines include the COS-7 line of monkey kidney cells (Gluzman et al., *Cell* 23:175 (1981)) and Chinese hamster ovary (CHO) cells. Expression of TRDL polypeptides in CHO cells is described below in Example 4.

The choice of a suitable expression vector for expression of TRDL polypeptides will of course depend upon the specific mammalian host cell to be used, and is within the skill of the ordinary artisan. Examples of suitable expression vectors include pcDNA3 (Invitrogen) and pSVL (Pharmacia Biotech). Expression vectors for use in mammalian host cells may include transcriptional and translational control sequences derived from viral genomes. Commonly used promoter sequences and enhancer sequences which may be used in the present invention include, but are not limited to, those derived from human cytomegalovirus (CMV), Adenovirus 2, Polyoma virus, and Simian virus 40 (SV40). Methods for the construction of mammalian expression vectors are disclosed, for example, in Okayama and Berg (*Mol. Cell. Biol.* 3:280 (1983)); Cosman et al. (*Mol. Immunol.* 23:935 (1986)); Cosman et al. (*Nature* 312:768 (1984)); EP-A-0367566; and WO 91/18982.

The polypeptides of the present invention may also be used to raise polyclonal and monoclonal antibodies, which are useful in diagnostic assays to for detecting TRDL polypeptide expression. Such antibodies may be prepared by conventional techniques. See, for example, *Antibodies: A Laboratory Manual*, Harlow and Land (eds.), Cold Spring Harbor Laboratory Press, Cold Spring Harbor, N.Y., (1988); *Monoclonal Antibodies, Hybridomas: A New Dimension in Biological Analyses*, Kennet et al. (eds.), Plenum Press, New York (1980).

The TRDL nucleic acid molecules of the present invention are also valuable for chromosome identification, as they can hybridize with a specific location on a human chromosome (described in Example 4). There is a current need for identifying particular sites on the chromosome, as few chromosome marking reagents based on actual sequence data (repeat polymorphisms) are presently available for marking chromosomal location. Once a sequence has been mapped to a precise chromosomal location, the physical position of the sequence on the chromosome can be correlated with genetic map data. The relationship between genes and diseases that have been mapped to the same chromosomal region can then be identified through linkage analysis, wherein the coinheritance of physically adjacent genes is determined. Whether a gene appearing to be related to a particular disease is in fact the cause of the disease can then be determined by comparing the nucleic acid sequence between affected and unaffected individuals.

Because TRDL is a new member of the TNF family of inflammatory cytokines, as demonstrated by the sequence homology between TDRL and TNF family members such as Fas ligand and TRAIL, it is likely that TRDL will elicit similar biological responses. These include activation of cellular apoptosis and activation of NFκB. Certain disease states exhibit a low level of apoptosis as compared to the level of apoptosis occurring in an individual not suffering from the disease. Such diseases include, e.g., cancers with p53 mutations, hormone-dependent tumors, autoimmune disorders and viral infections. Furthermore, as is described below in Example 2, certain tissue types exhibit higher levels of TRDL expression in normal tissue than in tumor tissue. Thus, one use for TRDL relates to a method for treating an individual in need of an increase in TRDL activity comprising administering to said individual TRDL, or an agent capable of decreasing TRDL activity (i.e., a TRDL agonist) to said individual. Administration of TRDL or a TRDL agonist may lead to the desired programmed cell death.

In addition, certain diseases involve an increased level of apoptosis as compared to the level of apoptosis occurring in an individual not suffering from the disease. Administration of TRDL or an agent that decreases TRDL activity (i.e., a TRDL antagonist) may therefore reduce the level of apoptosis in such an individual. Such diseases include, e.g., AIDS, neurodegenerative disorders, myelodysplastic disorders and ischemic injury. Thus, one use for TRDL relates to a method for treating an individual in need of a decrease in TRDL activity comprising administering to said individual an agent capable of decreasing TRDL activity (i.e., a TRDL antagonist) to said individual. Administration of a TRDL antagonist may lead to the desired programmed cell death.

Thus, in another embodiment, the invention relates to the use of TRDL polypeptides in the identification of TRDL agonists and antagonists. One such use of TRDL polypeptides is described in Example 5, below. In this example, cells bearing high affinity TRDL receptors are identified by combining labeled TRDL with different cell lines. The cell line expressing the highest level of TRDL binding is then used in high-throughput screening assays for TRDL agonists and antagonists as described below. An agent increasing TRDL binding to the cell line is thus a TRDL agonist, while an agent decreasing TRDL binding is a TRDL antagonist. Suitable labels for TRDL include biotin, radioisotopes such as $^{125}I$, $^{14}G$, $^{35}S$, and $^{3}H$, fluorescent labels such as fluoroscein and rhodamine, and enzymatic labels.

Thus, the invention provides a method for the identification of cells having a high affinity receptor for TRDL, the method comprising:
 (a) labeling an isolated TRDL polypeptide;
 (b) contacting the labeled TRDL polypeptide obtained in step (a)
  with cells of a mammalian cell line;
 (c) washing the cells obtained in step (b) to remove unbound TRDL; and
 (d) determining the presence of the labeled TRDL polypeptide in the washed cells obtained in step (c);
whereby the presence of labeled TRDL polypeptide in the washed cells obtained in step (c) indicates the presence of a high affinity receptor for TRDL on the cells.

In another embodiment, the invention relates to a method for the identification of an agent which inhibits the binding of TRDL to its receptor, the method comprising:
 (a) labeling an isolated TRDL polypeptide;
 (b) contacting the labeled TRDL polypeptide obtained in step (a)
  with cells of a mammalian cell line
  (i) in the presence of a test agent; and
  (ii) in the absence of a test agent;
 (c) washing the cells
  (i) obtained in step (b)(i); and
  (ii) obtained in step (b)(ii) to remove unbound TRDL;
 (d) determining the amount of labeled TRDL polypeptide in
  (i) the washed cells obtained in step (c)(i); and
  (ii) the washed cells obtained in step (c)(ii); and
 (e) comparing the amount of labeled TRDL polypeptide determined in step (d)(i) to that determined in (d)(ii);
whereby a lower amount of labeled TRDL polypeptide in sample (d)(i) than in sample (d)(ii) indicates that said agent inhibited the binding of TRDL to its receptor.

In another embodiment, the invention relates to a method for the identification of an agent which enhances the binding of TRDL to its receptor, the method comprising:
 (a) labeling an isolated TRDL polypeptide;
 (b) contacting the labeled TRDL polypeptide obtained in step (a)
  with cells of a mammalian cell line
  (i) in the presence of a test agent; and
  (ii) in the absence of a test agent;
 (c) washing the cells
  (i) obtained in step (b)(i); and
  (ii) obtained in step (b)(ii) to remove unbound TRDL;
 (d) determining the amount of labeled TRDL polypeptide in
  (i) the washed cells obtained in step (c)(i); and
  (ii) the washed cells obtained in step (c)(ii); and
 (e) comparing the amount of labeled TRDL polypeptide determined in step (d)(i) to that determined in (d)(ii);
whereby a higher amount of labeled TRDL polypeptide in sample (d)(i) than in sample (d)(ii) indicates that said agent has enhanced the binding of TRDL to its receptor.

Furthermore, as is described above, it is likely that TRDL will demonstrate activities common to the TNF family of cytokines, such as induction of apoptosis or prevention of apoptosis. Assays to be used for quantitation of cells having undergone apoptosis are well known in the art (See, e.g., Wiley et al., *Immunity* 3:673–682 (1995); Idziorek et al., *J. Immuno. Meth.* 185:249–258 (1995); X. M. Wang, et al., *Human Immunol* 37: 264 (1993)). Thus, by using an assay such as the DNA laddering apoptosis assay or the percent viability assay described in Wiley et al., or the cell death assay of Idziorek et al. (See Example 6), it will be possible to test the effect of TRDL on apoptosis induction or prevention in a variety of cell types, allowing identification of cell types which undergo programmed cell death upon interaction with TRDL, and of cell types which are prevented from undergoing programmed cell death upon interaction with TRDL.

Therefore, the invention provides a method for the identification of a cell line that undergoes apoptosis upon interaction with TRDL, the method comprising:

(a) dividing the cells of a culture of a mammalian cell line into a test culture and a control culture;

(b) contacting a TRDL polypeptide with the test culture of step (a);

(c) determining the quantity of cells of
  (i) the test culture obtained in step (b); and
  (ii) the control culture of step (a);
    that have undergone apoptosis; and (d) comparing the quantity of cells determined to have undergone apoptosis in the test culture of step (c)(i) with the quantity of cells determined to have undergone apoptosis in the control culture of step (c)(ii);

whereby a determination that the quantity of cells having undergone apoptosis in said test culture is higher than in said control culture indicates that said mammalian cell line undergoes apoptosis upon interaction with TRDL.

A mammalian cell line identified by the above method to undergo apoptosis upon interaction with TRDL may then be used in the identification of agents capable of inhibiting or enhancing TRDL-mediated induction of apoptosis. Therefore, the invention provides a method for the identification of an agent capable of inhibiting TRDL-mediated induction of apoptosis, said method comprising (a) determining the quantity of cells that have undergone apoptosis in a test culture and a control culture, wherein said test culture comprises mammalian cells capable of undergoing apoptosis upon interaction with TRDL which have been contacted with a TRDL polypeptide in the presence of a test agent, and said control culture comprises mammalian cells capable of undergoing apoptosis upon interaction with TRDL which have been contacted with a TRDL polypeptide in the absence of a test agent; and (b) comparing the quantity of cells determined to have undergone apoptosis in the test culture of step (a) with the quantity of cells determined to have undergone apoptosis in the control culture of step (a); whereby a determination that the quantity of cells having undergone apoptosis in said test culture is lower than in said control culture indicates that said test agent inhibits TRDL-mediated induction of apoptosis.

The invention also provides a method for the identification of an agent capable of enhancing TRDL-mediated induction of apoptosis, said method comprising (a) determining the quantity of cells that have undergone apoptosis in a test culture and a control culture, wherein said test culture comprises mammalian cells capable of undergoing apoptosis upon interaction with TRDL which have been contacted with a TRDL polypeptide in the presence of a test agent, and said control culture comprises mammalian cells capable of undergoing apoptosis upon interaction with TRDL which have been contacted with a TRDL polypeptide in the absence of a test agent; and (b) comparing the quantity of cells determined to have undergone apoptosis in the test culture of step (a) with the quantity of cells determined to have undergone apoptosis in the control culture of step (a);

whereby a determination that the quantity of cells having undergone apoptosis in said test culture is higher than in said control culture indicates that said test agent enhances TRDL-mediated induction of apoptosis.

Another activity exhibited by certain members of the TNF family of cytokines is the prevention of apoptosis. One example may be found in the interaction of tumor necrosis factor with the TNF receptor 2 (TNFR2). That interaction results in the removal of inhibition of NFκB, a transcription factor which, when activated, results in the protection of the cell from apoptosis.

Therefore, the invention provides a method for the identification of a cell line that is prevented from undergoing apoptosis upon interaction with TRDL, the method comprising:

(a) dividing the cells of a culture of a mammalian cell line into a test culture and a control culture;

(b) contacting a TRDL polypeptide with the test culture of step (a);

(c) determining the quantity of cells of
  (i) the test culture obtained in step (b); and
  (ii) the control culture of step (a);
    that have undergone apoptosis; and (d) comparing the quantity of cells determined to have undergone apoptosis in the test culture of step (c)(i) with the quantity of cells determined to have undergone apoptosis in the control culture of step (c)(ii);

whereby a determination that the quantity of cells having undergone apoptosis in said test culture is lower than in said control culture indicates that said mammalian cell line is prevented from undergoing apoptosis upon interaction with TRDL.

A mammalian cell line identified by the above method to be prevented from undergoing apoptosis upon interaction with TRDL may then be used in the identification of agents capable of inhibiting or enhancing TRDL-mediated prevention of apoptosis. Therefore, the invention provides a method for the identification of an agent capable of inhibiting TRDL-mediated prevention of apoptosis, said method comprising:

(a) determining the quantity of cells that have undergone apoptosis in a test culture and a control culture, wherein said test culture comprises mammalian cells that are prevented from undergoing apoptosis upon interaction with TRDL which have been contacted with a TRDL polypeptide in the presence of a test agent, and said control culture comprises mammalian cells that are prevented from undergoing apoptosis upon interaction with TRDL which have been contacted with a TRDL polypeptide in the absence of a test agent; and (b) comparing the quantity of cells determined to have undergone apoptosis in the test culture of step (a) with the quantity of cells determined to have undergone apoptosis in the control culture of step (a);

whereby a determination that the quantity of cells having undergone apoptosis in said test culture is higher than in said control culture indicates that said test agent inhibits TRDL-mediated prevention of apoptosis.

The invention also provides the invention provides a method for the identification of an agent capable of enhancing TRDL-mediated prevention of apoptosis, said method comprising (a) determining the quantity of cells that have undergone apoptosis in a test culture and a control culture, wherein said test culture comprises mammalian cells that are prevented from undergoing apoptosis upon interaction with TRDL which have been contacted with a TRDL polypeptide in the presence of a test agent, and said control culture comprises mammalian cells that are prevented from undergoing apoptosis upon interaction with TRDL which have been contacted with a TRDL polypeptide in the absence of a test agent; and (b) comparing the quantity of cells determined to have undergone apoptosis in the test culture of step (a) with the quantity of cells determined to have undergone apoptosis in the control culture of step (a);

whereby a determination that the quantity of cells having undergone apoptosis in said test culture is lower than in said control culture indicates that said test agent enhances TRDL-mediated prevention of apoptosis.

Having generally described the invention, the same will be more readily understood by reference to the following examples, which are provided by way of illustration and are not intended as limiting.

EXAMPLES

Example 1

Isolation and Sequencing of a Gene Encoding TRDL

Material and Methods (a) BLAST Searches of the Incyte Database: The Incyte LifeSeq database was searched using the basic local alignment search tool (BLAST) and the complete human TNF-α: cDNA sequence (Accession #M10988) as the query (Altschul, S. F., Gish, W., Miller, W., Myers, E. W., and Lipman, D. J. (1990) Basic local alignment search tool. *J. Mol. Bio.* 215, 403–410). Altschul, S. F., Gish, W., Miller, W., Myers, E. W., and Lipman, D. J. (1990) Basic local alignment search tool. *J. Mol. Bio.* 215, 403–410.

(b) Sequence Analysis: All nucleotide sequences were obtained directly using an ABI373A fluorescence-based sequencer (Perkin Elmer/Applied Biosystems Division, PE/ABD, Foster City, Calif.) and the ABI PRISM™ Ready Dye-Deoxy Terminator kit with Taq FS™ polymerase. Each ABI cycle sequencing reaction contained about 0.5 µg of plasmid DNA. Cycle-sequencing was performed using an initial denaturation at 98° C. for 1 min, followed by 35 cycles: 96° C. for 15 sec, annealing at 50° C. for 10 sec, and extension at 60° C. for 4 min. Temperature cycles and times were controlled by a Perkin-Elmer 9600 thermocycler. Extension products were purified using Centrisep gel filtration cartridges (Princeton Separation Systems, Adelphia, N.J.). Each reaction product was loaded by pipette onto the column, which was then centrifuged in a swinging bucket centrifuge (Sorvall model RT6000B table top centrifuge) at 1500×g for 4 min at room temperature. Column-purified samples were dried under vacuum for about 40 min and then dissolved in 3 µl of a DNA loading solution (83% deionized formamide, 8.3 mM EDTA, and 1.6 mg/ml Blue Dextran). The samples were then heated to 90° C. for three min and loaded into the gel sample wells for sequence analysis by the ABI373A sequencer (stretch modification). Sequence analysis was done by importing ABI373A files into the Sequencher program (Gene Codes, Ann Arbor, Mich.). Generally, sequence reads of 700 bp were obtained. Potential sequencing errors were minimized by obtaining sequence information from both DNA strands and by re-sequencing difficult areas using primers at different locations until all sequencing ambiguities were removed. The above methods, along with the LifeSeq Assembly function for the clones in cluster 99092, including clone 78258, allowed a contiguous 709 bp cDNA sequence to be obtained (FIG. 2). Included in the sequence is clone 798247, which lies furthest upstream in the contig.

Results and Discussion

A BLAST search of the Incyte LifeSeq long-read database using the entire protein coding region of human TNFα (Accession #M10988) as the query identified 7 matches of statistical relevance 30 (P<1.0) (12). Altschul, S. F., Gish, W., Miller, W., Myers, E. W., and Lipman, D. J. (1990) Basic local alignment search tool. *J. Mol. Bio.* 215, 403–410. Of these matches, 78258R1 displayed homology with TNFα in regions where TNFα was also homologous with FasL (Fas ligand) and TRAIL (TNF-related apoptosis-inducing ligand) (FIGS. 1A and 1B). A BLAST search of the entire Incyte LifeSeq database using clone 78258R1 identified 23 matches of statistical relevance (P<1.0) (Altschul, S. F., Gish, W., Miller, W., Myers, E. W., and Lipman, D. J. (1990) Basic local alignment search tool. *J. Mol. Bio.* 215, 403–410), 8 of which were identified as human CpG island DNA genomic MseI fragments. Analysis of the 23 matches revealed that 16 belonged to the same cluster as clone 78258. Assembly of cluster 99092, which contains 78258, produced a contiguous 709 base pair cDNA sequence. This contig was made up of several overlapping clones, including 798247 (from cDNA library OVARNOT03, nontumorous ovarian tissue) which appeared furthest upstream (FIG. 2), and retained homology with TNFα, FasL & TRAIL. The 798247 EST sequence available was limited to 285 bp and included a stop codon at the 3' end, but lacked a putative initiation methionine. In order to confirm 798247 as a TNFα homolog, the clone was obtained from Incyte for complete sequence analysis.

Sequence analysis of 798247 in pSPORT (Bethesda Research Laboratories, Bethesda, MD) identified an insert of 828 bp that contained a partial open reading frame of 172 amino acids. Although this clone retained the regions of homology with TNFα, the sequence for 798247 lacked a putative start methionine at the 5' end. This observation necessitated additional cloning experiments to obtain a full length clone and complete characterization.

Two full length clones for 798247 were obtained by screening $5\times10^5$ plaques from a leukocyte cDNA library. Primary screening identified 5 plaques that hybridized on duplicate lifts. Four of the five were subsequently plaque purified and insert sizes determined by PCR. Insert sizes ranged between 1.5 and 1.8 kb. Sequence analysis of 2 of the clones, TRDL-14 and TRDL-11, in pDR2 (Clontech, Palo Alto, Calif.) identified one insert of 1408 bp that contained a putative open reading frame of 248 amino acids, and another insert of 1537 bp that contained a putative open reading frame of 235 amino acids. Clones 14 and 11 were nearly identical, with the exception of a 48 base pair in-frame insertion that encodes sixteen amino acids (residues 111–127) present in clone 14 which is absent from clone 11. Sequence analysis of clones #11 and #14 revealed several differences from the 798247 sequence that appear to arise from alternative splicing of the TRDL gene. Furthermore, an exon of 183 base pairs was present at the 3' end of clone 11 which did not exist in clone 14. Both clones shared near identity with the original clone 798247, and with a contig assembled from Incyte clusters 99092 and 51748. FIG. 6 shows the protein alignment of clones TRDL-14 and TRDL-11 with TNF family members.

Another BLAST search against the full length sequence of clone TRDL-14 revealed a second cluster of clones which overlapped the 5' end of the original contig. When assembled, this cluster (51748) produced a 670 bp contig made up of 39 clones. When the 2 clusters were forced into a single assembly, the 3' end of the contig of cluster 51748 overlapped with the 5' end of the contig of cluster 99092, forming a new contig (881955) of 1136 base pairs, and providing an N-terminus which was missing from the original contig.

TRDL shares limited sequence homology with other TNF-related ligands. Sequence conservation with molecules like TNF, TRAIL and FasL was confined primarily to two short stretches within 100 amino acids from the carboxy terminus. The identification of these short, C-terminal stretches of identity allowed selection of the original BLAST match as a possible candidate despite poor statistical scores. The overall percent identity of the C-terminal domain of TRDL to TNFα, FasL and TRAIL is 17%, 17% and 12%, respectively. Although not striking, this level of homology is typical of the TNF cytokine family. By comparison, TRAIL is only 28% homologous to FasL, 23% homologous to TNFα and 22% homologous to lymphotoxin β. Like these family members, TRDL contains a putative transmembrane segment near the N-terminus that is likely required for proper presentation of this molecule on cell surfaces (Wiley, S. R., Schooley, K., Smolak, P. J., Din, W. S., Huang, C-P., Nicholl, J. K., Sutherland, G. R., Davis Smith, T., Rauch, C., Smith, C. A., and Goodwin, R. G. (1995) Identification and characterization of a new member of the TNF family that induces apoptosis. *Immunity.* 3, 673–682).

Example 2

Tissue Distribution of TRDL Expression

Material and Methods (a) Preparation of pDR2/TRDL: The conversion from a λDR2 to a 5 pDR2 plasmid was carried out in AM1 cells as described in Clontech Protocol #PT1011-1. Plasmid DNA was purified by Qiagen mini- or maxi-prep (Qiagen, Chatsworth, Calif.).

(b) Northern Analysis: An Incyte Electronic Northern was run on clones 798247 (from cluster 99092) and 177393 (from cluster 51748). This function displays an Electronic Northern and has two objectives: to determine the libraries in which a given gene is expressed and its abundance levels in each one. In the LifeSeq database, this analysis is based on master cluster membership. Clone 177393 was selected because its sequence represents the 5' end of pDR2/TRDL-14.

Multiple human tissue mRNA blots were purchased from Clontech Laboratories (Palo Alto, Calif.). Plasmid DNA (pSPORT/798247) was digested with NotI+SalI, purified by QIAquick Gel Extraction Kit (Qiagen, Chatsworth, Calif.), and labeled with $\alpha$c32PdCTP using a multiprime labeling kit (Ready-to-go DNA labeling kit, Pharmacia Biotech). The blot was hybridized at 68° C. for 2.5 h in Express Hyb buffer (Clontech, Palo Alto, Calif.). Unbound probe was removed by 3 quick rinses then two 20 min washes at room temperature in 2×SSC, 0.05% SDS, followed by two 30 min washes at 50° C. in 0.1×SSC, 0.1% SDS. Hyperfilm MP (Amersham) was exposed overnight at −80° C.

A human cancer cell line multiple tissue mRNA blot was purchased from Clontech (Palo Alto, Calif.). The first approximately 700 bp of the coding region of pDR2/TRDL-14 were PCR amplified using primers which were 5'-ATATGGATCCC-AGCTCATGCCAGCCTCA-3' (SEQ ID NO:12) and 5'-AGTAAAGCTTGGAATTATG-ACACTCAGAATATCCC-3' (SEQ ID NO:13). The gel-purified PCR product was labeled for use as a probe, and the blot was hybridized as described above.

(c) Dot Blot Analysis: A tumor gene screening 96 dot total RNA dot blot was purchased from Biochain Institute, Inc (San Leandro, Calif.). The blot was hybridized concomitantly with the cancer cell line northern blot.

(d) Screening of Leukocyte Library: Screening of Clontech human leukocyte library HL1169X (λDR2) was carried out as described in the Clontech Lambda Library Protocol Handbook (PR92192). Labeled 798247 probe was produced using Ready-to-go Beads (Pharmacia Biotech) and $\alpha^{32}$PdCTP (Amersham). Primary screening of $5 \times 10^5$ plaques identified 5 plaques that hybridized on duplicate lifts. Four of the five were plaque purified in 2° and 3° screens, and insert sizes were determined by PCR.

Results and Discussion

Results of Incyte LifeSeq Electronic northerns for clones 798247 and 177393 are shown in FIG. 7. These results indicate that the DNA sequences represented by these 2 clones are expressed mainly in inflammatory tissues, tumors, and tissues with an abundant peripheral blood supply.

Figure 8A:
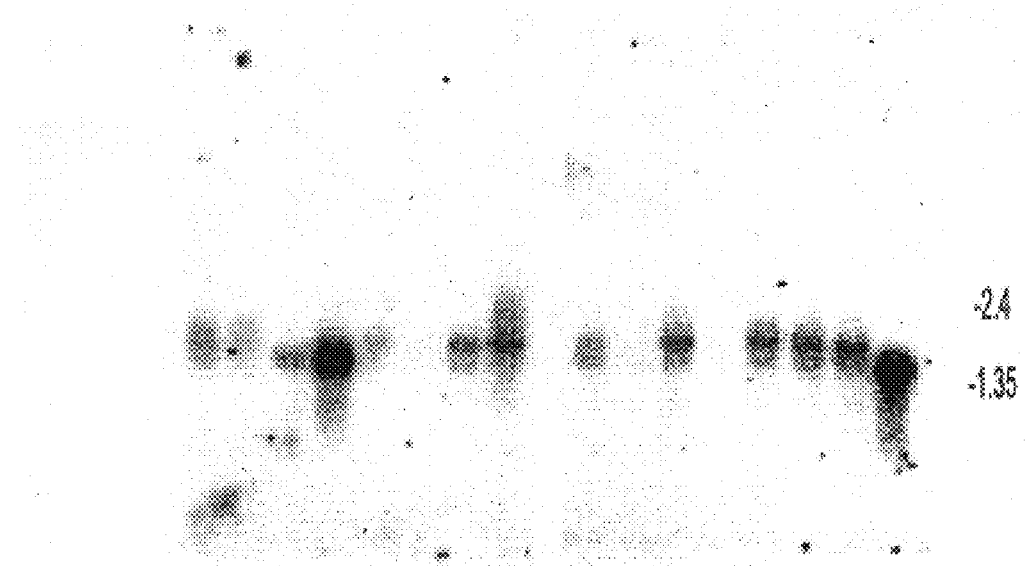
FIGS. 8A and 8B.
Figure 8B:
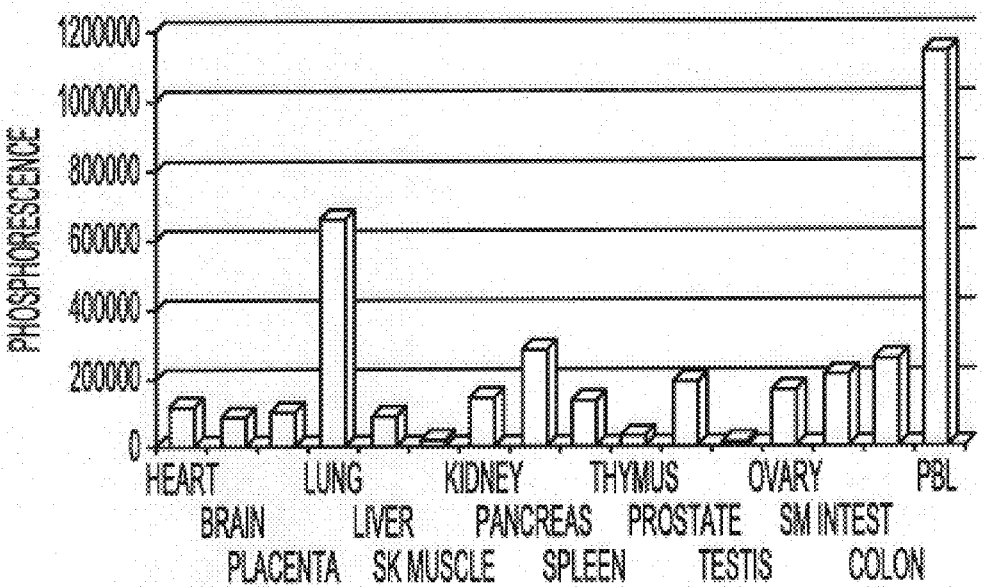

The tissue distribution of 798247 was determined by Northern analysis of mRNA isolated from multiple tissues. Hybridization with the full length 798247 insert (cut out of pSPORT w/ SalI & NotI) identified two RNA species at approximately 1.6 and 1.8 kb. Highest levels of expression were seen in lung and peripheral blood leukocytes, with intermediate levels of expression in pancreas, colon, small intestine, prostate and ovary. There was little or undetectable expression in skeletal muscle, thymus, and testis (FIGS. 8A and 8B).

Figure 9A:
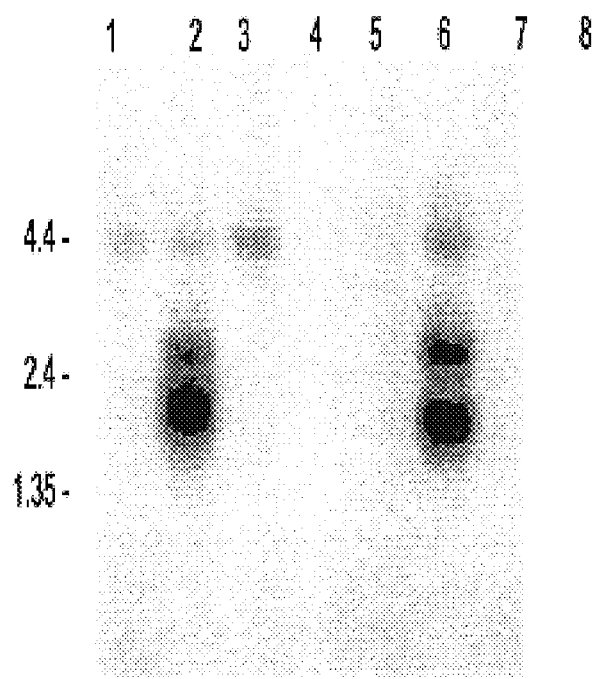
FIGS. 9A and 9B.
Figure 9B:
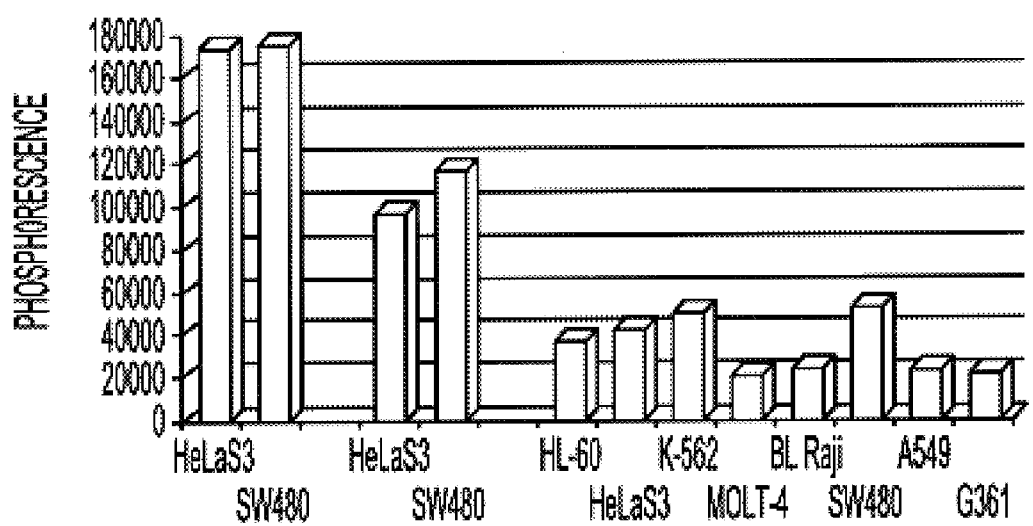

A Northern blot of human cancer cell lines was hybridized using the first approximately 700 bp of the coding region of clone TRDL-14. Highly expressed RNA species were identified at 1.7 kb, 2.5 kb in HeLa and SW480 cells. A third species at 4.4 kb was moderately expressed in HeLa, SW480, HL-60, and K-562 cells (FIGS. 9A and 9B).

Figure 10A:
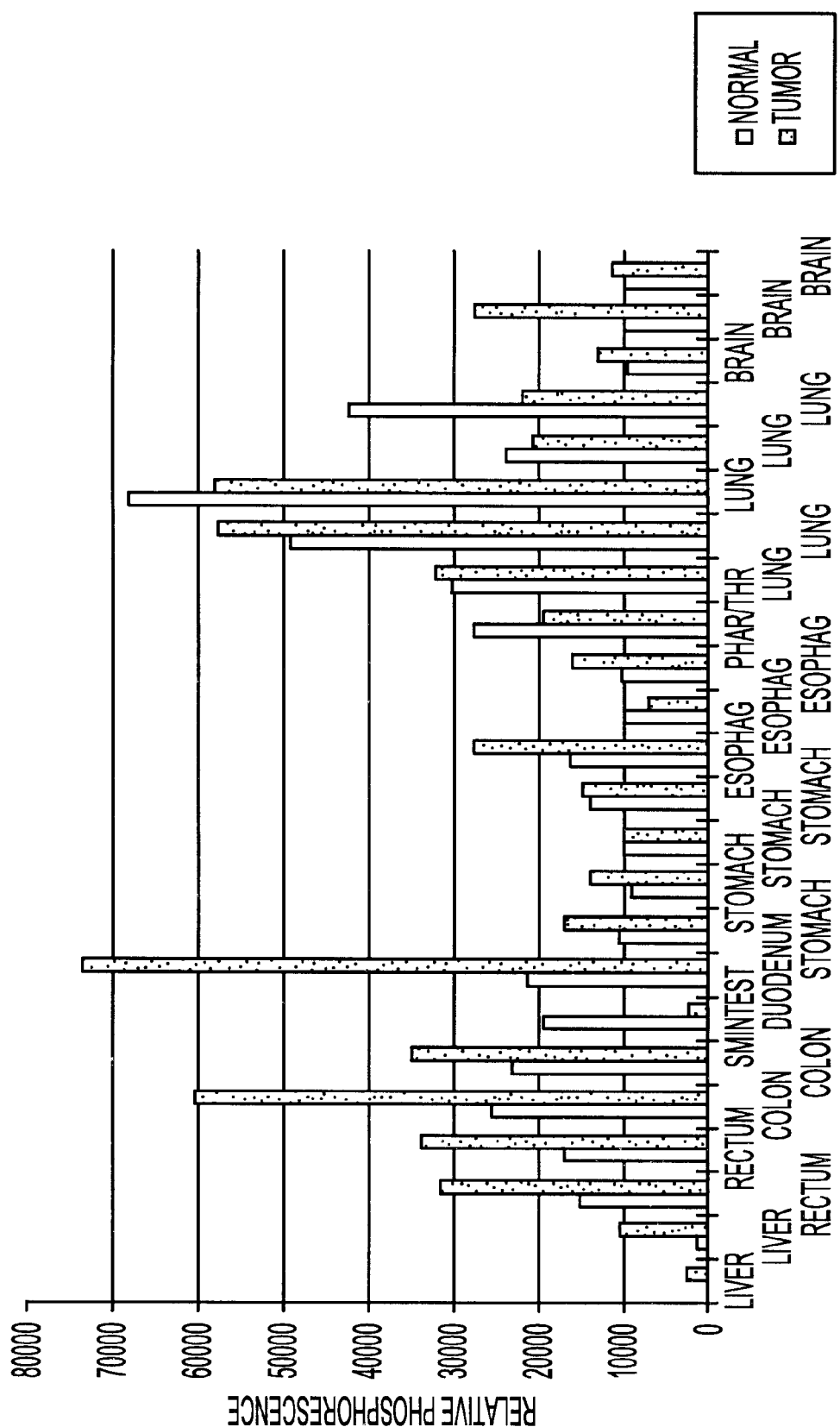
FIGS. 10A and 10B.
Figure 10B:
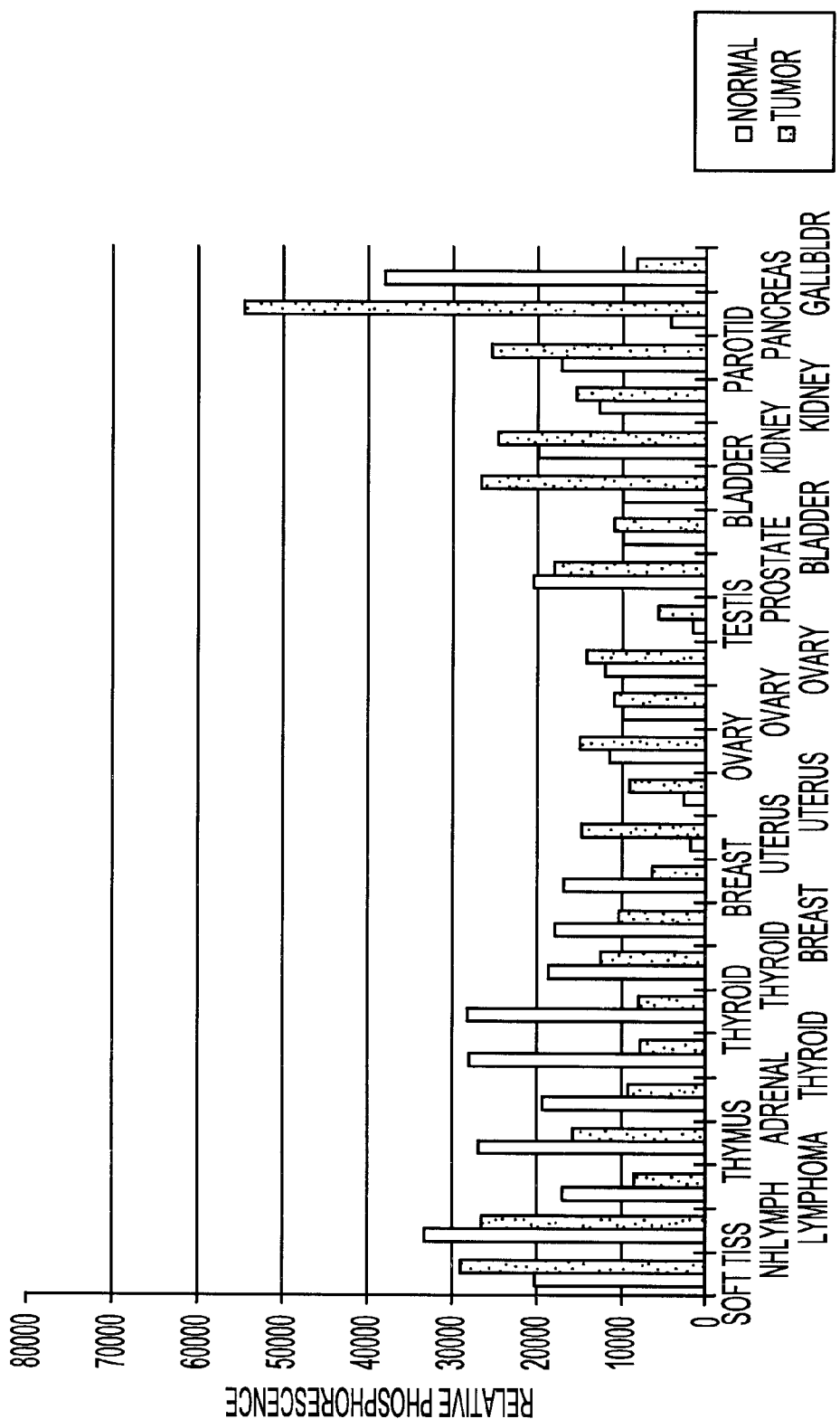

A tumor gene screening RNA dot blot was also hybridized using the TRDL-14 probe. Highest levels of expression were seen in tumor samples compared with normal samples of duodenum, colon, and pancreas. By contrast, expression was higher in normal than in tumor samples in tissues such as gallbladder, thyroid, small intestine, thymus, adrenal and breast. Expression in lung was high in both normal and tumor samples (FIGS. 10A and 10B).

Evidence for alternative splicing was seen via northern analysis using RNA isolated from multiple human tissues. Lung and peripheral blood leukocytes showed high levels of expression of a 1.6 kb transcript only. In contrast, a low level, 1.8 kb transcript appeared in tissues like kidney, pancreas and prostate. This size difference is consistent with the 183 bp exon missing from clone pDR2/TRDL-14, and may correspond to the two transcript sizes seen in tissues. Two transcripts were also seen in northern analyses of tumor cell lines. In this case, both transcripts were present in the same cell lines. Thus, tissues with the highest expression levels lung and peripheral blood leukocytes) appear to selectively generate the 1.6 kb transcript. In contrast, tissues with low level of TRDL expression produce the 1.8 kb message. This differential expression suggests alternative splicing as a mechanism for tissue-specific expression and functional regulation.

The expression profile of TRDL was similar but not identical to the expression profile of other TNF-related cytokines. The recently described TRAIL ligand, for example, showed levels of expression in lung and peripheral blood leukocytes that were similar to that seen in other tissues (Wiley, S. R., Schooley, K., Smolak, P. J., Din, W. S., Huang, C-P., Nicholl, J. K., Sutherland, G. R., Davis Smith, T., Rauch, C., Smith, C. A., and Goodwin, R. G. (1995) Identification and characterization of a new member of the TNF family that induces apoptosis. *Immunity.* 3, 673–682). In cancer cell lines, expression of TRDL was primarily limited to HeLa (cervical cancer) and SW480 (colorectal cancer) cell lines, again pointing to a potential for cell specific expression of this gene. Electronic northern analysis of TRDL using the Incyte database revealed an expression pattern that adds to the interest in this molecule as an inflammatory mediator. At least one EST corresponding to TRDL was identified in 42 different libraries. Of these, 24 ESTs appeared in inflamed tissues or tumors. This confirms the presence of TRDL in target disease states.

Example 3

Heterologous expression of TRDL
Materials and Methods (a) pcDNA3/TRDL-14 Expression in *E. coli:* The polymerase chain reaction was utilized to amplify the full length coding region of TRDL-14 from pDR2/TRDL-14 using BamHI and EcoRI modified primers. The primers used were 5'-CAGCTCA-TGCCAGCCTCA-3' (SEQ ID NO:14) and 5'-TATCCGTAAAATCAAAGTCCCAG-3' (SEQ ID NO: 15), purchased from Genosys Biotechnologies, Inc. (The Woodlands, Tex.). 10 ng of plasmid served as the template under the following PCR conditions: 30 cycles (30 sec at 94° C.; 1 min at 55° C.; 1 min at 72° C.). The product was subcloned using a SureClone kit (Pharmacia Biotech). DH5α competent cells (GIBCO-BRL) were transformed and plasmid DNA was purified (Qiagen, Chatsworth Calif.). The insert was removed by BamHI and EcoRI digestion and transferred to pcDNA3 (Invitrogen, Carlsbad Calif.). DH5α competent cells were transformed and positive colonies determined by PCR analysis. Plasmid DNA from positive colonies was purified (Qiagen) and insert sequence confirmed using an ABI373A fluorescence based sequencer as described above.

(b) Expression of Human TRDL in CHO cells: The complete open-reading frame of human TRDL was expressed in Chinese hamster ovary (CHO) cells under the control of the CMV immediate early promotor. Plasmid pDR2/TRDL14 was double digested with XbaI and BamHI and the resulting cDNA fragment was ligated into XbaI and BamHI digested pUC18 to yield pUC18-TRDL14. pUC18/TRDL14 was the double digested with EcoRI and BamHI and the resulting DNA fragment was ligated to EcoRI and BamHI digested pcDNA3 to yield pcDNA3/TRDL14. pcDNA3/TRDL14 was then used to transfect CHO K1 cells using Lipofectamine and stable transfectants were isolated following neomycin selection (G418 0.8 μg/ml). Clonal cell lines were prepared by limiting dilution.

The predicted extracellular domains of human TRDL-11 and human TRDL-14 were engineered by PCR for expression as NH$_2$-terminal fusions with a 6 His-tag in the baculovirus transfer vector pAcHLT-A. A common 5' sense oligonucleotide primer (5'-CATATGCACAGAGCTGCAGAGCCTCAGGAG-3' (SEQ ID NO:16), base pairs 217–239 in TRDL-14 and 226–248 in TRDL-11) containing a NdeI restriction site was paired with 3' antisense primers specific for either TRDL-11 or TRDL-14 and containing KpnI sites in the PCR (5'-TCACAGTTTCACAAACCCCAGGAAG-3' (SEQ ID NO:17) and 5'-GTAAAATCAAAGTCCCAGGAAGGT-3' (SEQ ID NO:18), corresponding to base pairs 781–804 and 750774 in TRDL-14 and TRDL-11, respectively). pDR2/TRDL14 plasmid DNA or pDR2/TRDL11 plasmid DNA (0.1 μg) was amplified using the sense and antisense primers (1 μM) and the Pwo thermostable polymerase under the following cycle conditions; denature for 1 min at 94° C., anneal for 2 min at 65° C., and extend for 3 min at 72° C. for 20 cycles. The resulting products were digested to completion with NdeI and KpnI and ligated into NdeI and KpnI digested baculovirus transfer vector pAcHLT-A to yield pAcHLT-A/TRDL14 and pAcHLT-A/TRDL11. Both expression plasmids were completely sequenced on both strands to confirm the integrity of the open-reading frame.

(c) Expression of Human TRDL in baculovirus: Baculovirus transfer vectors containing either human TRDL-11 (pAcHLT-A/TRDL11) or human TRDL-14 (pAcHLT-A/TRDL14) were co-transfected with BaculoGold™ DNA into Sf9 cells using standard transfection procedures. Intracellular expression was confirmed by metabolic labeling of the cells during infection followed by SDS-PAGE analysis. Five distinct virus plaques were cloned and analyzed for TRDL expression to obtain a single high producing viral isolate. An amplified virus stock then used to infect approximately 1×10$^9$ cells in Grace's serum-free medium/ liter of either Sf9 cells or Hi5 cells with 5 PFU/cell. Following 65 hr in shaker flasks, the infected cells were harvested by centrifugation and the cell lysate served as the starting material for purification using Ni-agarose.

(d) Engineering of the extracellular domain for secretion from sf9 cells: The predicted extracellular domain of human TRDL11 and human TRDL14 was engineered for secretion from sf9 cells by preparing an in-frame fusion with the honey bee melatin leader sequence in the baculovirus transfer vector pVT-Bac (Tessier, D. C., Thomas, D. Y., Khouri, H. E., Laliberte, F., and Vernet, T. , *Gene* 98:177–183 (1991)). Sense and antisense PCR primers, incorporating restriction sites for directional cloning into pVT-Bac, were used to amplify the region of the TRDL11 or TRDL14 coding sequences corresponding to the extracellular domain as indicated above. The amplification products were then digested to completion with the appropriate restriction endonucleases and subcloned into pVT-Bac. Expression of pVT-Bac/TRDL11 and pVT-Bac/TRDL14 by cotransfection with BaculoGold DNA was performed as described above.

(e) Isolation of human TRDL genomic clones: A partial cDNA clone of human TRDL was used to isolate bacterial artificial chromosome (BAC) genomic clones by colony hybridization. The cDNA insert was random prime labeled with α-$^{32}$P-dATP and used to screen a human BAC genomic library. Individual clones were isolated by dilution plating and rescreening and two clones were obtained, 14814 and 14815. PCR analysis using oligonucleotide primers specific for either the shared exon or the TRDL-14/TRDL-11 exons confirmed that both BAC clones contain the entire open-reading frame of human TRDL.

Example 4

Human Chromosomal Mapping of Human TRDL by Fluorescence in situ Hybridization

DNA from clone 14815 was labeled with digoxigenin dUTP by nick translation. The labeled probe was combined with sheared human DNA and hybridized to normal metaphase chromosomes derived from phytohemagglutanin (PHA)-stimulated peripheral blood lymphocytes in a solution containing 50% formamide, 10% dextran sulfate and 2×SSC. Specific hybridization signals were detected by incubation with fluoreseinated antidigoxigenin antibodies followed by counterstaining with 4',6-diamidine-2'-phenylindole dihydrochloride (DAPI) for one color experiments. Probe detection in two color experiments was accomplished by incubation with fluoresceinated antidigoxigenin antibodies and Texas rad avidin followed by counterstaining with DAPI. The initial experiment resulted in specific labeling of the short arm of a group E chromosome which was believed to be chromosome 17 on the basis of size, morphology and banding pattern. A second experiment was conducted in which a biotin labeled probe specific for the centromeric region of chromosome 17 was cohybridized with clone 14815. This experiment resulted in the specific labeling of the centromer in red and the short arm of chromosome 17 in green. Measurements of 10 specifically labeled chromosomes 17 demonstrated the 14815 is located at a position which is 77% of the distance from the centromere to the telomere of chromosome arm 17p in an area which corresponds to band 17p13.3. A total of 80 metaphase cells were analyzed with 72 exhibiting specific labeling.

Hypermethylation of CpG islands located within the upstream sequences of vertebrate genes has potential gene silencing consequences. Several studies have demonstrated hypermethylation of CpG islands on human Chromosome 17p13.3 in tumor DNA compared to normal DNA in both colon, breast, and prostate (Ribieras et al., *J. of Cellular Biochemistry* 56:86–96 (1994); Morton, R. A., et al., *J. Urology* 156:512–516 (1996)). An essential role for NF-κB in preventing TNF-α-induced cell death. *Science.* 274:782–784). Furthermore, CpG islands within the TRDL gene have led to the annotation of some TRDL ESTs as CpG islands. Thus, it is possible that hypermethylation and consequent inactivation of the TRDL gene results in cancer.

Example 5

High Through-Put Screens for TRDL Agonists and Antagonists

Materials and Methods (a) Preparation of radiolabeled human TRDL: The soluble extracellular domain of human TRDL is expressed as an amino terminal 6-His-tagged fusion using baculovirus as described above. Material produced by the infected cells is recovered from the cells by hypotonic lysis/homogenization followed by affinity chromatography on a Ni-NTA agarose. The purified protein is then eluted from the affinity resin using imidazole containing buffer and stored frozen in aliquots prior to use.

A sample of the purified TRDL protein radiolabeled with $^{125}I$ using iodogen. Iodogen (10 μl of a 1.0 mg/ml solution in $CHCl_3$) is evaporated under nitrogen, mixed with 30 μl of 1.0 M $KPO_4$ (pH 7.0)/10 μl (1.0 mCi) of $Na^{125}I$ and incubated for 10 minutes on ice. This mixture is transferred to a tube containing 10 μg of human TRDL in 20 μl and reacted for 5 minutes on ice. Unincorporated $Na^{125}I$ is removed using a PD10 column equilibrated with PBS/0.1% gelatin.

(b) Development of a receptor binding assay and high through-put screening: $^{125}I$-TRDL is used to survey human cell lines for the presence of high affinity receptors [U937, THP-1, Jurkat, HeLa and SW480]. Triplicate tubes containing $1.0 \times 10^5$ cells are incubated with $2.0 \times 10^5$ dpm of $^{125}I$-TRDL in the absence or presence of increasing amounts of unlabeled TRDL over the range 0–10 nM in a total volume of 0.5 ml RPMI 1640 medium/2% FCS. After 2 hr on ice, the cells are washed 3× with 10 ml fresh medium and cell associated TRDL are quantified by γ-counting.

High through-put screening is done using the scintillation proximity assay (SPA). Membranes prepared from the cell line expressing the highest level of TRDL receptors are coated onto SPA beads by incubation on ice for 1 hour. Membrane-coated SPA beads are mixed with $^{125}I$-TRDL and incubated for 30 minutes at room temperature. The SPA beads are then washed with PBS and scintillation detected using a scintillation spectrometer. For screening, the SPA binding assay are performed in the presence or absence of test compounds (10 μM), and agents that reduce the SPA signal by >50% under these conditions are scored as positive.

Example 6

Assay for the Quantitation of Cell Death

Cell death assay: Cell death is quantitated using the DNA binding dye, YOPRO-1 (Molecular Probes, Junction City, Oreg.) (Idziorek, T.,et al., *J. Immuno. Meth.* 185:249–258 (1995). Confluent, serum-starved MCF7 cells in 24-well plates are treated with either UV or etoposide for 16 hours. 1 μM YOPRO-1 is then incubated with the cells at 37° C. for 60 minutes. YOPRO-1 uptake is assessed by reading the plate in the fluorescent plate reader at 460 nm excitation and 585 nm emission.

It will be clear that the invention may be practiced otherwise than as particularly described in the foregoing description and examples.

Numerous modifications and variations of the present invention are possible in light of the above teachings and, therefore, are within the scope of the invention.

The entire disclosure of all publications cited herein are hereby incorporated by reference.

What is claimed is:

1. An isolated nucleic acid molecule comprising a polynucleotide having a sequence selected from the group consisting of:
   (a) a nucleotide sequence encoding a TNF-related death ligand polypeptide having the complete amino acid sequence of SEQ ID NO:2 or SEQ ID NO:4;
   (b) a nucleotide sequence encoding the extracellular region of a TNF-related death ligand polypeptide having the amino acid sequence at about position 53 to about position 234 of SEQ ID NO:2, or about position 53 to about position 247 of SEQ ID NO:4; and
   (c) a nucleotide sequence fully complementary to the nucleotide sequence of (a) or (b).

2. The nucleic acid molecule of claim 1, wherein said polynucleotide molecule of 1(a) has the nucleotide sequence given in SEQ ID NO:1 or SEQ ID NO:3.

3. The nucleic acid molecule of claim 1, wherein said polynucleotide molecule of 1(b) has the nucleotide sequence given in SEQ ID NO:1 from about nucleotide 226 to about nucleotide 771, or the nucleotide sequence given in SEQ ID NO:3 from about nucleotide 217 to about nucleotide 801.

4. A vector comprising the nucleic acid molecule of claim 1.

5. The vector of claim 4, wherein said nucleic acid molecule of claim 1 is operably linked to a promoter for the expression of a TNF-related death ligand polypeptide.

6. A host cell comprising the vector of claim 4.

7. A host cell comprising the vector of claim 6.

8. The host cell of claim 7, wherein said host is a eukaryotic host.

9. The host cell of claim 8, wherein said host cell is a baculovirus cell.

10. The host cell of claim 8, wherein said host cell is a CHO cell.

11. A method of obtaining a TNF-related death ligand polypeptide comprising culturing the host cell of claim 7 and isolating said TNF-related death ligand polypeptide.

12. The isolated nucleic acid of claim 1 wherein said polynucleotide molecule of 1(a) is identical to a sequence encoding a TNF-related death ligand polypeptide having the complete amino acid sequence of SEQ ID NO:2.

13. The isolated nucleic acid of claim 1 wherein said polynucleotide molecule of 1(a) is identical to a sequence encoding a TNF-related death ligand polypeptide having the complete amino acid sequence of SEQ ID NO:4.

14. The isolated nucleic acid of claim 1 wherein said polynucleotide molecule of 1(b) is identical to a sequence encoding a TNF-related death ligand having the amino acid sequence of about position 53 to about position 234 of the SEQ ID NO:2.

15. The isolated nucleic acid of claim 1 wherein said polynucleotide molecule of 1(b) is identical to a sequence encoding a TNF-related death ligand having the amino acid sequence of about position 53 to about position 247 of SEQ ID NO:4.

16. The isolated nucleic acid of claim 1 wherein said polynucleotide molecule of 1(c) is fully complementary to a polynucleotide which is identical to a sequence encoding a TNF-related death ligand polypeptide having the complete amino acid sequence of SEQ ID NO:2.

17. The isolated nucleic acid of claim 1 wherein said polynucleotide molecule of 1(c) is fully complementary to a polynucleotide sequence encoding a TNF-related death ligand polypeptide having the complete amino acid sequence of SEQ ID NO:4.

18. The isolated nucleic acid of claim 1 wherein said polynucleotide molecule of 1(c) is fully complementary to a polynucleotide sequence encoding a TNF-related death ligand having the amino acid sequence of SEQ ID NO:2 from between about position 53 to about position 234.

19. The isolated nucleic acid of claim 1 wherein said polynucleotide molecule of 1(c) is fully complementary to a polynucleotide sequence encoding a TNF-related death ligand having the amino acid sequence of SEQ ID NO:4 from between 53 to about position 247 of SEQ ID NO:4.

* * * * *